United States Patent [19]
Theimer et al.

[11] 3,966,972
[45] June 29, 1976

[54] PACKAGED COATED FOOD PRODUCT CAPABLE OF BEING COOKED USING ELECTRODES

[75] Inventors: Ernst Theodore Theimer, Rumson; George E. Heinze, East Brunswick, both of N.J.

[73] Assignee: Lectrofood, Inc., East Brunswick, N.J.

[22] Filed: Feb. 28, 1974

[21] Appl. No.: 446,822

[52] U.S. Cl. .................................. 426/90; 99/358; 252/518; 426/92; 426/107; 426/234; 426/573; 426/575
[51] Int. Cl.² ...................... B65B 25/22; A23L 1/04
[58] Field of Search ........... 426/107, 244, 245, 246, 426/234, 89, 90, 92, 302–304, 305, 129, 573, 575, 641, 645, 523; 99/358; 252/518

[56] References Cited
UNITED STATES PATENTS

| | | | |
|---|---|---|---|
| 2,306,573 | 12/1942 | Stern | 99/358 |
| 2,582,174 | 1/1952 | Spencer | 426/243 |
| 2,939,793 | 6/1960 | Richman | 426/245 |
| 3,053,667 | 9/1962 | Luijerink | 426/246 |
| 3,062,663 | 11/1962 | Furgal et al. | 426/107 X |
| 3,230,861 | 1/1966 | Korr | 99/358 |
| 3,245,338 | 4/1966 | Korr | 426/107 X |
| 3,311,285 | 3/1967 | Korr | 99/358 |
| 3,548,738 | 12/1970 | McDevitt | 99/358 X |
| 3,565,642 | 2/1971 | Hirsch | 99/358 |
| 3,873,742 | 3/1975 | Miyahara | 426/234 |
| 3,886,290 | 5/1975 | Theimer et al. | 426/107 |

FOREIGN PATENTS OR APPLICATIONS

| | | | |
|---|---|---|---|
| 45-17131 | 6/1970 | Japan | 426/244 |
| 47-1813 | 1/1972 | Japan | 426/244 |

OTHER PUBLICATIONS
Modern Packaging, pp. 94, 95, 4/57.

*Primary Examiner*—Steven L. Weinstein
*Attorney, Agent, or Firm*—Arthur L. Liberman

[57] ABSTRACT

Described is a packaged food product, including a container, shell or enclosure which exists in an "open" position prior to loading and "closed" position thereafter and which encloses relatively high electrically conducting and low electrically conducting food substances such that the relatively low electrically conducting food component has in contact therewith on at least one of its surfaces or envelopes the major part of the relatively high electrically conducting food component. The high conducting food substance can protrude or extend longitudinally away from the substantially diametrically opposite ends of the low conducting food substance or it can be totally enclosed in the low conducting food substance. When the container, shell or enclosure is in a closed position, both the low conducting and high conducting food substances are held in a fixed position as a result of the design of the internal surfaces of the ends of one or both portion(s) of the container, enclosure or shell. At the ends of the container, enclosure or shell, electrical conducting means, such as metal foils, are attached to and are in intimate contact with the internal surfaces of diametrically opposite ends of the container and are designed to make electrical contact with the terminals of an electrical energy source for a finite period of time when the container is in a closed position and while the foods are held in the container. In common contact with the electrically conducting means and that surface of the conducting food through which it is intended to pass the electrical current, is a gel and ionized species.

15 Claims, 31 Drawing Figures

FIG.6
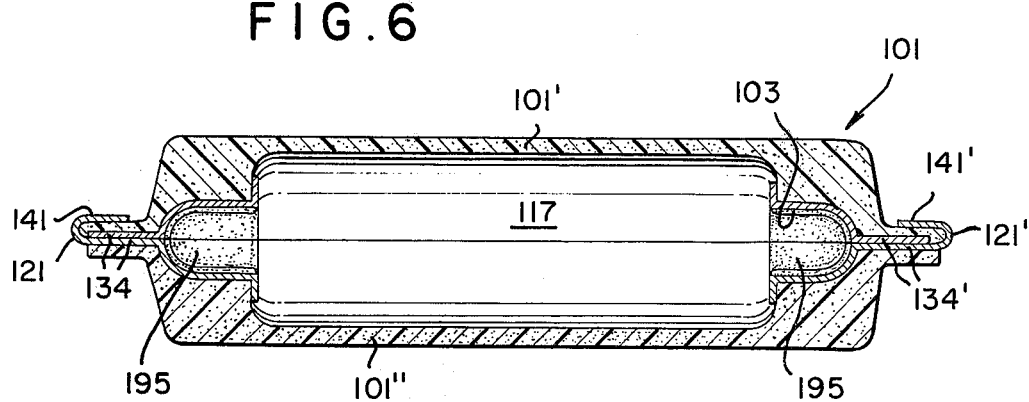
FIG.7
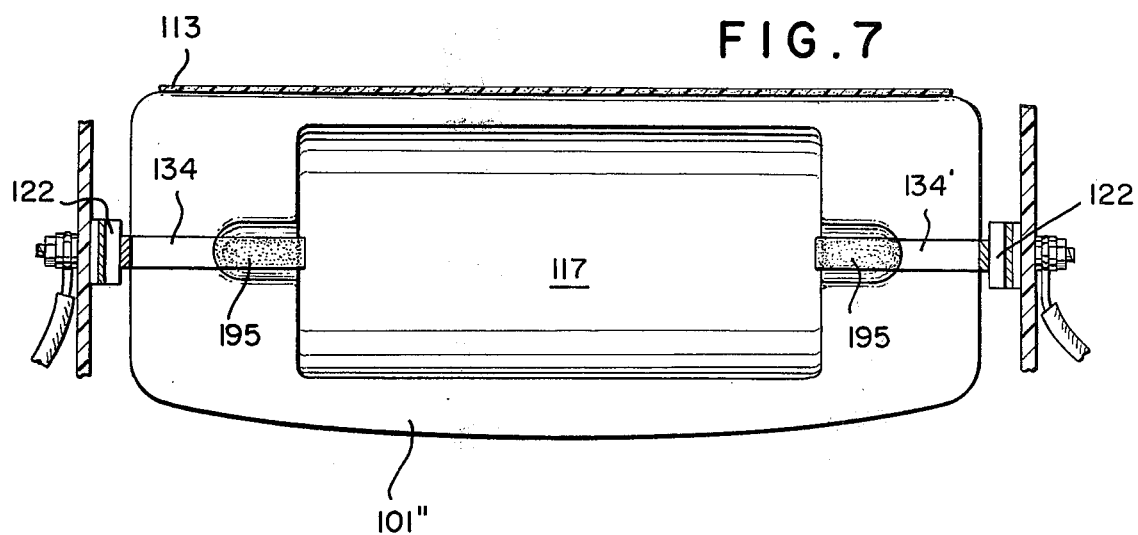
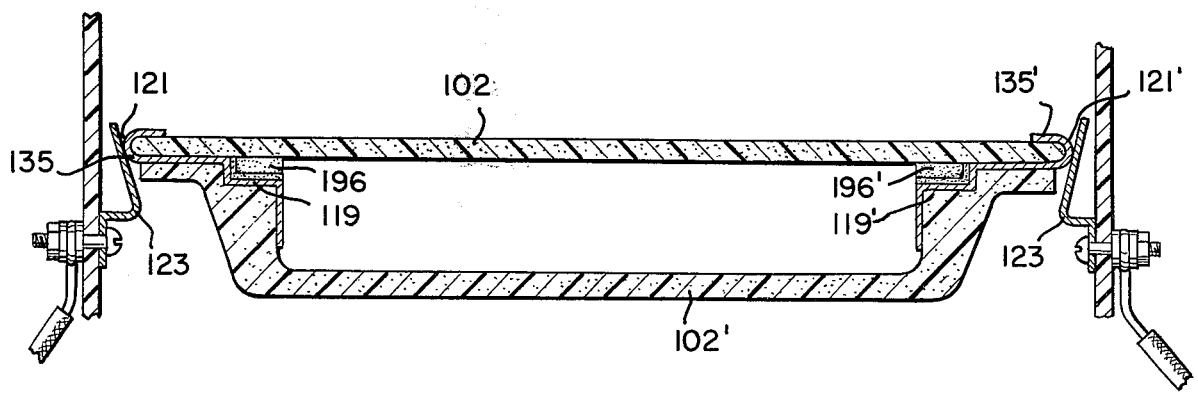
FIG.8

PACKAGED COATED FOOD PRODUCT CAPABLE OF BEING COOKED USING ELECTRODES

BACKGROUND OF THE INVENTION

This invention relates to an edible electrically high conducting food substance having:
a. Substantially diametrically opposite ends,
b. At least one substantially solid surface,
c. At least two electrical contacts located at said substantially diametrically opposite ends of said food substance, and in contact with said substantially solid surface; and
d. At least a major portion of said substantially solid surface having in intimate contact therewith a composition comprising:
   i. A gel; and
   ii. A substantially ionized species.

The invention also covers the aforementioned composition comprising the gel and the substantially ionized species. In addition, this invention also relates to a unit food package such as a unit sausage (e.g. frankfurter), pizza, hamburger, or cheeseburger package and more particularly to a unit moisture-containing compound food package in which an electrically conducting food such as a frankfurter, which is in intimate contact and within or upon a suitable non-electrically conductive food substance such as a bun, may be cooked without arcing occurring and caused to remain conveniently hot throughout and palatable for a convenient period of time after cooking. This invention also relates to the container used for enclosing the electrically non-conductng food and electrically conducting food, the said container being an integral part of said compound food unit.

BACKGROUND: DESCRIPTION OF THE PRIOR ART

The cooking of an electrically conducting food substance by passing an electrical current therethrough, i.e., by means of electrical resistance cooking, is known, as shown by the following United States patents:

U.S. Pat. No. 3,651,752, incorporating by reference Application for U.S. Letters Patent, Serial Number filed June 30, 1969.
   Inventor: Roslonski
   discloses: a package food product such as a frankfurter having a wrapper. The wrapper ends have two separate conducting strips which contact two portions of the food substance for cooking same. The wrapper is sealed about the ends of the food substance allegedly to insure good electrical contact between the conducting strips and the food substance.

U.S. Pat. No. 2,939,793.
   Inventor: Richman
   discloses: a frankfurter package unit including a frankfurter axially confined in a wrapper, the frankfurter having its pulp portion exposed at both ends at right angles to its longitudinal axis within the wrapper, the wrapper consisting of sealed end portions formed of flexible metallic electrical conducting material secured at opposite end portions to a central non-conducting wrapper material, the trimmed ends of the frankfurter being in juxtaposition to the sealed metallic conductor ends of the wrapper whereby the frankfurter can be cooked without removing the wrapper, by insertion of the entire package intermediate to a pair of electrodes and applying electrical current through the electrodes in sufficient amount to heat the frankfurter without the electrodes perforating the wrapper.

U.S. Pat. No. 3,548,738.
   Inventor: McDevitt
   discloses: a hot dog vending machine including a cold food storage compartment, a pair of vertically spaced actuating bars and a composite hot dog - electrode cooking package stored within the food compartment with special emphasis on the nature of the package, which package includes a pair of spaced electrodes each of which is bonded to the hot dog and retained within a cylindrical cadboard container previously formed for operation in the machine and cooperating with the spaced actuating bars. The electrodes may be in the form of end caps which fit in intimate contact over the ends of the frankfurter and which do not puncture the frankfurter. See Column 3, lines 60 – 66.

U.S. Pat. No. 3,886,290
   Inventors: Ernst Theodore Theimer Donald Joseph Roslonski
   discloses: a packaged food product comprising:
   a. An electrically low conducting food;
   b. An electrically high conducting food disposed in proximate contact with said low conducting food;
   c. Said high conducting food having two axially polar high conducting food portions having external surfaces and extending outwardly beyond said low conducting food;
   d. Enclosing said low conducting food, a hollow thermally insulating substantially moisture-impervious container for holding said electrically low conducting food, said container being capable of existing in a closed position and in an open position, said container comprising two sections having substantially conterminous edges, a first section and a second section articulating said first section, said first section and said second section having mutually substantial continuous co-extensive edges, at least of one said sections having an internal surface designed to fixedly hold said food over a substantial portion of the surfaces of said food when the container is in a closed position;
   e. At least one of said container sections having axially polar ends, said axially polar ends having internal axially polar surfaces which are co-extensive with the external surface of said axially polar high conducting food portions;
   f. Electrical conducting means extending outwardly from said container, said electrical conducting means having electrical conducting ends external to said container, said ends being designed to make electrical contact with the terminals of an electrical energy source when said container is in a closed position, said electrical conducting means being affixed to each of said internal axially polar surfaces, said electrical conducting means being in intimate electrical contact with the external surfaces of said two axially polar high conducting food portions when said container is in a closed position.

One of the principal advantages of this type of electrical resistance cooking is the relatively short period of time required for conducting food substances to be effectively cooked thereby. Accordingly, electrical resistance cooking has been taught to be employed preferentially in food dispensing machines where speed of cooking is particularly desirable.

One of the most common conducting food substances cooked by electrical resistance cooking in dispensing machines is the frankfurter. Prior to the above-named invention of Theimer and Roslonski, a frankfurter pierced at each end by an electrode was cooked by passing an electrical current between the electrodes. Usually, the frankfurter is disposed within a bun, and the resulting sandwich enclosed by a wrapping having suitable openings for admitting the electrodes therein. The principal disadvantage of employing a package of this type is that the food substances within the package are exposed to the surrounding atmosphere and thus subject to contamination.

One solution to this problem was to enclose associated conducting and non-conducting food substances, i.e. a frankfurter and bun, in a wrapper having conducting portions which contact the conducting food substance so that electrical current may be passed through such substance without disturbing the integrity of the wrapper. A packaged food product of this type is disclosed in Richman U.S. Pat. No. 2,939,793. However, new problems were posed by this packaging technique, namely the difficulty of maintaining good electrical contact between the conducting portions of the wrapper and the conducting food substance and unacceptable arcing and resultant burning which occurred during the cooking operation. One solution to this problem, offered in the aforementioned Richman patent, was to lay bare as by peeling the ends of the conducting food substance to expose the inner portions thereof. Such exposed inner portions are then placed in intimate contact with the conducting portions of the wrapper.

However, this solution is essentially inoperable using the method described in Richman, and further, using the technique described in Roslonski, or that shown in FIG. 9 of McDevitt since the contact area (in each of the disclosures) between electrode and frankfurter is too small to permit rapid cooking without charring of the meat. In addition, baring the ends of the frankfurter as done by Richman, is a costly, unhygienic and superfluous operation. Further, encasing each end of both the conducting food and non-conducting food (which encloses the conducting food), as described in Roslonski, leads to inefficiency and inconvenience to the consumer of the product. A further disadvantage when using the Roslonski product is that some of the foil may adhere to the food product when the package is opened for eating. The electrode caps of McDevitt (FIG. 9) must be removed prior to removal of the food product from the McDevitt vending machine. This aspect of McDevitt leads to much inconvenience on the part of both the vendor and the vendee of the McDevitt food unit.

Another solution offered by the Theimer and Roslonski invention partly solved the foregoing problems but did not completely obviate the problem of arcing and resultant burning during the electrical resistance cooking operation.

SUMMARY OF THE INVENTION

The present invention offers a convenient, economically attractive solution to the above-mentioned problems. Basically, the electrically high conducting food substance of our invention has:
a. Substantially diametrically opposite ends;
b. At least one substantially solid surface;
c. At least two electrical contacts located at said substantially diametrically opposite ends of said food substance and in contact with said substantially solid surface; and
d. At least a major portion of said substantially solid surface having in intimate contact therewith a composition comprising:
i. A gel; and
ii. A substantially ionized species.

The composition of our invention which is to be in intimate contact with the solid surface with the electrically high conducting food substance of our invention comprises:
i. An aqueous gel selected from the group consisting of agar, xanthan gum, tragacanth, guar gum, gum arabic, and algin gum, in water; and
ii. A substantially ionized species selected from the group consisting of sodium chloride, potassium chloride, ammonium chloride, sodium iodide, potassium iodide, magnesium chloride, sodium glutamate, potassium glutamate, sodium alginate, potassium alginate, ammonium alginate, magnesium alginate, calcium alginate, sodium bicarbonate, potassium bicarbonate, magnesium bicarbonate, calcium bicarbonate, sodium nitrate, potassium nitrate, sodium nitrite and potassium nitrite.

Basically, the food package of our invention comprises:
a. An electrically high conducting food substance having at least one substantially solid surface;
b. At least two electrical contacts located at substantially diametrically opposite ends of said food substance; and
c. A composition, as described above, comprising:
i. An edible gel; and
ii. An edible ionic species
said composition being positioned to make intimate contact between the electrically high conducting food substance and the two electrical contacts.

The electrically high conducting foodstuff of our invention preferably has an electrical resistivity in the range of from 1 to 50 ohm inches over a temperature range of from 30° F up to 250° F. Electrically high conducting foodstuffs having such physical properties are exemplified by the following:
1. Ground meat patties;
2. Sausage
3. Pizza topping
4. Kielbasa
5. Blintzes
6. Egg rolls
7. Cold cuts
8. Cold cuts-cheese combination, and
9. Cold-cut chopped liver combination The electrically high conducting food substance of our invention preferably has coated thereon a composition wherein the weight ratio of gel to substantially ionized species is from about 1:20 up to about 20:1. The composition comprising the gel and the ionized species may either be an integral part of discrete portions of the substantially solid surface of the electrically high conducting food substance or it may be coated onto only discrete portions of the substantially solid surface of the electrically high conducting food substance, or it may be coated onto each of the two electrical contacts, or it may be coated onto i. each of the surfaces of the two electrical contacts; and in addition ii. discrete portions of the substantially solid surface of the electrical high conducting food substance, preferably only in the proximate regions where the electrical contacts contact the electrically high conducting food substance.

More specifically, the edible electrically high conducting composition of our invention is intended to form a continuous phase on dry out. The composition of the coating initially comprises:

i. From 86 up to 99.3 weight percent water;

ii. From 0.5% up to 4.0% by weight of the said edible gel; and iii. From 0.2% up to 10.0% by weight of the edible ionized species.

In addition, and preferably, the packaged food product comprises:

a. An electrically low conducting food having high electrical resistivity;

b. An electrically high conducting food disposed in proximate contact with said low conducting food;

c. Said high conducting food having at least two substantially diametrically opposite high conducting food portions, having substantially solid external surfaces;

d. In common intimate contact with at least two portions of at least one of the external surfaces of said high conducting food, 1. An electrically high conducting composition comprising:
   i. A gel; and
   ii. An edible non-toxic ionic species;

2. At least two electrical contacts Said composition being positioned to make intimate contact between the two electrical contacts and the substantially solid surface of said electrically high conducting food;

e. Enclosing said low conducting food, a hollow thermal insulating substantially moisture impervious container for holding said electrically low conducting food, said container being capable of existing in a closed position and in an open position, said container comprising two sections having substantially conterminous edges, a first section and a second section articulating said first section, said first section and said second section having mutually substantially continuous conterminous edges, at least one of said sections having an internal surface designed to fixedly hold said food over those portions of the external surfaces of said food which are in intimate contact with said electrically high conducting composition and said electrical contacts when the container is in a closed position.

Further preferred is such a packaged food product wherein:

a. At least one of said container sections has substantially diametrically opposite internal surfaces which are conterminous with the external surfaces of said diametrically opposite high conducting food portions; and b. The electrical contacts extend outwardly from said container, said electrical contacts having electrically conducting ends external to said container, said ends being designed to make electrical contact with an electrical energy source when said container is in a closed position.

The above-mentioned packaged food product may be modified so that said first section of said container and said second section of said container have mutually substantially continuous co-extensive edges which edges are interrupted at the proximate regions of said substantially diametrically opposite high conducting food portions such that discrete container openings exist at said proximate regions whereby said electrical contacts have means of egress from said container when said container is in a closed position.

More particularly the enclosure part of the packaged food product of our invention consists of an electrically and thermally non-conducting shell, the internal ends of which are form-fitting to the protruding ends of the electrically conducting food substance. In addition, the said container, enclosure or shell may also be form-fitting to a minor part of the non-conducting food substance. A significant part of the form-fitting portion of the said shell may be lined with an electrical conducting means adhering thereto, such as a conducting film (e.g. by means of aluminum metallizing or foil) which preferably extends to the exterior of the shell or is attached to a second electrical conducting foil section or wire which extends to the exterior of the container at each end, or from its sides, so as to effect electrical contact with the electrodes of a cooking device without requiring the physical opening of the container or the physical penetration of the container during cooking. Metallizing can be effected according to any of the processes set forth in U.S. Pat. No. 3,533,828; 3,549,505; or 3,669,714.

A container, as described above for the purposes of our invention, is fabricated of an electrically and thermally insulating material such as cardboard, or preferably a rigid polymer, such as polyvinyl chloride or polyvinyl acetatepolyvinyl chloride copolymer, or an aerated polymer such as polystrene or polyurethane in order to provide a light, disposable package suitable for use in vending machines and for large scale food vending operations where it is desirable to cook rapidly large quantities of units and keep them reasonably warm for relatively long periods of time subsequent to cooking. Examples of such vending machines are set forth in U.S. Pat. No. 3,651,752 issued on Mar. 28, 1972. In particular, such a container, shell or enclosure would be operable whereby when an electrical current in the initial range of 1.0 to 10.0 amperes and from 100 up to 500 volts is applied for a period of time from 3 up to 20 seconds to an electrical conducting means, the food product within the container (e.g. a frankfurter having a diameter of ⅝–⅞ inch and being 4.5–6 inches in length) being cooked internally so that the average temperature of the electrically conducting food (such as a frankfurter) after cooking, is initially in the range from 140° F to 212° F and the average temperature range of the accompanying low conducting food (e.g. a frankfurter roll, hamburger bun or pizza dough) is, after cooking, initially in the range of 100° F to 160° F; and after about 50 minutes after cooking the average temperature of the high conducting food is in the range of from 100°F to 150°F and the average temperature of the low conducting food is from 90°F to 130°F. The container described herein accomplishes this, and in addition, obviates the need to expose fresh portions of the electrically conducting food (as, for example, by cutting or peeling the ends of a frankfurter) thereby (1) maintaining proper hygienic standards; (2) simplifying the packaging and (3) improving the accessibility of the food to the consumer.

When used in conjunction with the composition of our invention, coated onto the electrical contacts or the high conducting food substance, or both, the problem of undesirable arcing and consequent spot burning of the food is completely obviated, thereby improving the desirablity of the food from the consumer's standpoint and also improving the continuity of heat storage in the food substance.

When the container is fabricated from a yielding material such as, preferably styrofoam (aerated polystyrene) or rigid polyvinyl chloride-polyvinyl acetate copolymer, the act of closing the container onto the food material in the initial packaging operation insures the necessary intimate contact between the internal surfaces of the substantially diametrically opposite ends of the container and the surface of the electrically conducting food substance (e.g. the frankfurter) at the ends thereof without danger of damage to the food. The rest of the container need not perform any function other than to (1) loosely enclose the food and (2) act as a thermal insulator subsequent to the cooking operation keeping the food in a conveniently warm state until it is eaten. The substantially diametrically opposite internal ends of the container may be lined with or may merely envelop electrically conducting means, preferably with an electrically conducting film such as a metallized aluminum surface or foil at least 0.2 mils in thickness ($2\times10^{-4}$ inches) which 1. Makes contact with the electrically high conducting food substances;
2. Extends or has an electrical connection from the ends, or the sides, to the outside of the container, shell or enclosure;
3. Is in contact with the composition of our invention comprising the gel and the ionized species which composition simultaneously is in contact with the electrically high conducting food substance; and
4. Makes contact during cooking with electrodes which are in turn in contact with an electrical energy source.

The electrical conducting means may be pinned or adhered to the internal end regions of the container in a form-fitting manner or may merely be enveloped by the container at the end regions thereof after the container is closed. In this manner a relatively large area of contact between the electrically conducting food and electrodes is provided without the need for an operation which involves physical intrusion into the closed container at any time subsequent to packaging and prior to opening the package to eat the cooked food. This obviously insures sanitary handling and simplifies the construction of the cooking device. The relatively large area of contact is essential to the success of rapid and effective cooking. The ratio of the contacted surface area of high conducting food portion to non-contacted surface area of high conducting food portion is preferably from about 1:50 up to 1:4. The term "contacted" is intended to mean "area of electrically high conducting food contacted by the electrical conducting means." Too small a contact area (below the ratio of 1:50) slows down the rate of cooking, leading to a heating time inconveniently long for the operation of our invention. Too high a contact area leads to a charring of the food.

While a major use of the special package is for cooked frankfurter, other foods may be cooked with equal effectiveness in other packages using the same principles. These include: hamburgers, cheeseburgers, sausages other than frankfurters, pizza, kielbasa, blinzes, knishes, kishka, "egg rolls", cold cuts (e.g. corned beef, pastrami and roast beef), cold cut-cheese combinations, and cold cut-chopped liver combinations.

When the electrical conducting means contacts a limited portion of the non-conducting food substance, i.e. frankfurter roll, or a hamburger bun or pizza dough, the roll becomes warm while the meat or pizza filling or the like is cooked more rapidly than otherwise, thus improving the palatability of the unit and permitting a longer period of time between cooking and consumption. Otherwise, heating of the non-conducting food is dependent upon heat conduction into it by means of the mass transfer of hot water vapor diffusing from the conducting food into the non-conducting food as the conducting food is heated. The operable and workable thickness range of the walls of the enclosure, shell or container used in conjuncton with our invention is from 0.01 inches up to 1 inch with 3/32–¼ inches preferred in the case of a foamed polymer such as styrofoam and from 0.01 up to 0.1 inches preferred in the case of a rigid polymer such as a polyvinyl acetate-polyvinyl chloride copolymer, for ease in handling and for optimal thermal performance. The thermal conductivity of the materials of construction of the container, shell or enclosure should be less than 1.50 BTU/hour-sq.ft.-(°F/inch). A practical thermal conductivity range when using a foamed polymer is from 0.15 up to 0.50 BTU/hour-sq.ft.-(°F/inch). The more preferable range of thermal conductivity of the foamed polymer-type materials of construction of the shell, enclosure or container of our invention is from 0.20 – 0.30 BTU/hour-sq.ft.-(°F/inch) at a mean temperature of between 60°F and 100°F. Thus, for example, a convenient and workable polystyrene foam for use as a material of construction may have at a mean temperature of 75°F the following thermal conductivity coefficients:

| | Density | K(BTU/hour-ft²-(°F/inch) |
|---|---|---|
| 1 | lb/ft³ | 0.26 |
| 1.5 | lb/ft³ | 0.25 |
| 2 | lb/ft³ | 0.24 |

A practical thermal conductivity range when using a thin wall (0.01–0.1 inch thickness) rigid polymr such as a polyvinyl chloride-polyvinyl acetate copolymer is from 1.0 up to 1.4 BTU/hour-sq.ft.-(°F/inch).

The container useful with our invention may be produced by means of vacuum forming or thermo-forming or by means of molding. Thus, for example, the thermo-formed container, shell or enclosure may be produced using rigid polymer or polymeric foam planar sheets of appropriate thickness wherein there is attached to said sheets metal foil strips in such a way that an excess of foil beyond the planar shape of the plastic is present, permitting the foil to follow the contours of the shaped plastic without tearing.

The composition of our invention comprising the gel and ionized species may be pre-coated onto the metal foil prior to or subsequent to the attachment of the metal foil to the polymer or prior to it being applied to the already-shaped plastic.

With the foregoing in mind, it is a primary object of the present invention to provide an improved packaged food product for use in hot food dispensing machines, an integral part of which is a specially designed article of manufacture, whereby during and subsequent to the electrical resistance, cooking the packaged food may be conveniently maintained in a heated state until its consumption.

It is a further object of this invention to provide an improved packaged food product containing an electrically high conducting food substance which can be heated and caused to remain in a heated state until consumption by means of electrical resistance cooking without the occurrence of undesired arcing and resultant spot burning during the cooking operation.

It is also an object of this invention to provide a packaged food product in which an electrically high conducting food substance is disposed in intimate contact with an electrically low conducting food with the high conducting food having two substantially diametrically opposite high conducting food portions substantially solid surfaces, substantially opposite regions of which are coated with a composition comprising a gel and an ionized species whereat an electrical current can be easily conducted into and out of the electrically high conducting food substance and which high and low conducting foods are contained in an enclosure or shell or container for enclosing the food during and subsequent to the electrical resistance cooking of same which is designed to:

1. Be thermally and electrically insulating;
2. Totally envelop the electrically low conducting food;
3. Have an internal surface fixedly holding the food over a significant portion of the surface of the food;
4. Have internal substantially diametrically opposite surfaces which are co-extensive with the external surfaces of diametrically opposite food ends; and
5. Have within the container, in intimate contact with the substantially diametrically opposite ends of the high conducting food (which have coated thereon or are in intimate contact with the composition comprising the gel and ionized species) electrical conducting means (such as aluminum metallizing aluminum foil) which extend outwardly from the container or shell or enclosure when it is in a closed position, which electrical conducting means are designed to make electrical contact with a source of electrical energy.

It is a further object of this invention to provide a container or shell or enclosure designed for enveloping an electrically low conducting food which is in contact with electrically high conducting food coated at its end regions with a composition comprising a gel and an ionized species which container or shell or enclosure is so designed that it is both thermally and electrically insulating and the container or enclosure or shell includes, as integral parts thereof, at least two separate electrical conducting means substantially at the ends thereof passing from the outside of the container or shell or enclosure, each of which means is caused by the container or enclosure or shell itself to be in intimate contact with the substantially diametrically opposite ends of the electrically conducting food (at the portions coated with the above-mentioned composition) intended to be cooked during the electrical resistance cooking operation.

It is a further object of our invention to provide a packaged food product (including an electrically conducting food substance in contact with an electrically non-conducting food substance) which food product is enveloped in an enclosure, shell or container specifically designed for maximum convenience in catering by (i) facilitating the passage without undesirable electrical arcing of an electrical current through the electrically conducting food substance for electrical resistance cooking of same, and (ii) simultaneously causing same to remain in a heated state for an extended period of time subsequent to the passage of said electrical current without exposing the said food substance to possible sources of contamination.

These and other objects of the invention will become apparent upon a consideration of the detailed description of preferred embodiments thereof given in connection with the following drawings.

DETAILED DESCRIPTION OF THE DRAWINGS

FIG. 1 is a front perspective view of that portion of our invention which constitutes the enclosure portion of the packaged food product, showing in an open position a hollow thermally insulating container or shell or enclosure 101 having a trough 117 therein for holding the electrically high conducting and electrically low conducting foods and having an internal surface 103 and 103' shaped to fixedly hold the end of the high conducting or low conducting food when the container or shell or enclosure is in a closed position, prior to, during and subsequent to the electrical resistance cooking operation. To obviate arcing the ends of the electrically high conducting food (e.g., frankfurter) where they contact the electrical contacts 134 and 134' are coated with the composition of our invention, the gel and the ionic species.

FIG. 2 is a front perspective view of our invention showing the packaged food product with the enclosure therefor 106 in an open position, wherein the enclosure is holding an electrically low conducting food (in this case hog dog bun) which is enveloping an electrically high conducting food (in this case a hot dog 112 having coated on its surface, which surface is contacted by the electrical contacts 134 and 134' a chemical composition comprising a gel and an ionic species).

FIG. 3 is a front perspective view of that part of our invention which shows the packaged food product consisting of the electrically low conducting food enveloping the electrically high conducting food having coated on its surface a composition comprising a gel and a ionized species, which electrically high conducting food is totally enclosed within a hollow thermally and electrically insulating container 101 and 101' with electrical contacts 134 (which are caused by the design of the container to be in intimate contact with the coated surface of the electrically high conducting food) connected to a source of electrical energy, during the cooking operation (not shown).

FIG. 4 is a longitudinal cross-sectional view taken along line 4—4 of FIG. 3 showing the electrically low conducting food 106 enveloping the electrically high conducting food 109 (which has its surface which is in contact with the electrical contacts 134 coated with a composiion 195 comprising a gel and an ionic species at regions 111 and 111') enclosed within the container, shell or enclosure 101' and 101" (which container, shell or enclosure is in a closed position). The electrically high conducting food is shown being cooked using the electrical contacts 134 (e.g., consisting of aluminum foil strips) which extend outwardly from the container or shell or enclosure at 141 and 141' and which are in electrical contact with the terminals 122 of an electrical energy source (not shown). composition FIG. 5 is a close-up longitudinal cross-sectional view of an end portion of the electrically low conducting food 106 enveloping an end portion of the electrically high conducting food 127 (which is coated with a composition 195 comprising a gel and an ionized species such as sodium chloride on that portion of its surface which is in contact with an electrical contact 134) enclosed within the container, shell or enclosure (which container, shell or enclosure is in a closed position). The electrically high conducting food is shown being cooked using the electrical contacts 134 (e.g., aluminum foil strips) which extend outwardly from the container or shell or enclosure and which are attached to the terminals (not shown) of an electrical energy source (also not shown).

FIG. 6 is a substantially similar view as shown in FIG. 4 wherein the enclosure or shell or container 101, the purpose of which is to envelope the low conducting food, has no food within it. In this case, however, the composition 195 which prevents arcing is coated on the internal surface 134 designed to fixedly hold the electrically high conducting food over those portions of the external surfaces of the food which are in intimate contact with the electrical contacts 134.

FIG. 7 is a longitudinal cross-sectional view taken along line 7—7 of FIG. 4 wherein the enclosure or shell or container 101 does not contain food but where the electrical contacts 134 are connected to the terminals of an electrical energy source 122.

FIG. 8 shows a longitudinal cross-sectional view of an empty container or shell or enclosure 102 and 102', the purpose of which is to envelope prior to, during and subsequent to electrical resistance cooking, an electrically low conducting food which has only one of its surfaces in intimate contact with an electrical high conducting food (such as in the case of a pizza slice or an open faced roast beef sandwich or an open base hamburger or cheeseburger). In common intimate contact with the ends of the electrically high conducting food (in regions 119 and 119') and the electrical contacts 135 and 135' is a composition 196 and 196' comprising an ionic species and a gel the presence of which composition prevents arcing during the electrical resistance cooking.

FIG. 9 is a longitudinal cross-sectional view of the packaged food product which is part of our invention wherein the electrically low conducting food 112 has only one of its surfaces 116 in intimate electrical contact with the electrically high conducting food 108 (as is the case when cooking pizza or an open face roast beef sandwich or an open face hamburger or cheeseburger) and wherein the electrical contacts 135 (such as aluminum metallizing or aluminum foil) adhering to the internal surfaces of the substantially diametrically opposite ends of the container or shell or enclosure 150 are caused as a result of the container or shell or enclosure design to be in intimate contact with the end portions of the electrically high conducting food surfaces. The electrical contacts 135 are in contact with an electrical energy source during the cooking operation through leads 123. In common contact with the ends of the electrically high conducting food and the electrical contact is a composition 196 comprising a gel (such as agar) and an ionized species (such as sodium chloride) the presence of which composition prevents arcing the electrically resistance cooking operation.

FIG. 10 represents a longitudinal cross-sectional view taken along line 10—10 of FIG. 9 wherein the enclosure, shell or container 102 for the electrically low conducting and electrically high conducting foods has no food therein and wherein the internal design of the container is specifically shaped for an electrically low conducting food having only one of its surfaces in contact with the electrically high conducting food, e.g., in the case of pizza or an open face cold cut sandwich or an open face hamburger or cheeseburger.

FIG. 11 is a front perspective view of that aspect of our invention which constitutes the enclosure portion 101' and 101" of the packaged food product showing a variation of the enclosure of FIG. 1, in an open position a hollow thermally insulated container or shell or enclosure 101' and 101" having a trough 117 therein for holding the electrically low conducting food, and having an internal surface 103 shaped to fixedly hold the ends of the food product when the container or shell or enclosure is in a closed position prior to, during and subsequent to the electrical resistance cooking operation. The electrical contacts 136 and 136' located at substantially diametrically opposite ends of the container (intended to be in intimate contact with the ends of the electrically high conducting food when the container is in a closed position) are placed such that their egress from the container is at the side of the container (at 147 and 147') rather than, as in FIG. 1, at the opposite ends of the container.

FIG. 12 is a front perspective view of the invention showing the packaged food product with the enclosure therefor 106 in an open position.

FIG. 13 is a front perspective view of the invention showing the packaged food product consisting of the electrically low conducting food enveloping the electrically high conducting food totally enclosed within a hollow thermally and electrically insulated container 101' and 101" with electrical contacts 136 and 136' (which contacts are caused by the design of the container or shell or enclosure to be in intimate contact with the electrically high conducting food at those surfaces of the electrically high conducting food which are coated with a composition comprising a gel and an ionized species) connected to a source of electrical energy during the cooking operation (not shown). The electrical contacts protrude from the sides of the container (at 147 and 147') rather than from the ends of the container as indicated in FIG. 3.

FIG. 14 is a front perspective view of the invention showing the packaged food product with an enclosure 117 therefor in an open position wherein the enclosure is holding an electrically low conducting food 106 (in this case the lower portion of the hog dog bun) which is enveloping an electrically high conducting food 109 (in this case a hot dog having a length which is less than the length of the electrically low conducting food). The electrically high conducting food 109 is being cooked using electrical contacts 136 and 136' (e.g., aluminum foil strips) which extend outwardly from the side of the container or shell or enclosure at 147 and 147' and which are attached to the terminals of an electrical energy source (not shown). The electrical contacts are affixed to the surface 211 and 211' of the electrically high conducting food at those regions of the surface of said high conducting food which are coated with a composition comprising a gel (such as agar) and an ionized species (such as sodium chloride) in order to eliminate arcing during the electrical resistance cooking operation.

FIG. 15 is a cross-sectional view taken along the line 15—15 of FIG. 14. The surface of the electrically high conducting food (in this case a hot dog) is coated with a composition 195 comprising a gel and an ionized species at that section 211 which is in common contact with the electrical contact.

FIG. 16 is a cross-sectional view taken along the line 15—15 of FIG. 14 but showing the composition 195 of the gel and ionized species as being coated on the electrical contact 136 rather than on the electrically conducting food substance as is the case in FIG. 15.

FIG. 17 is a front perspective view of that aspect of our invention which constitutes the enclosure portions of the packaged food product, showing in an open position a hollow thermally insulating container or shell or enclosure 301' and 301" having a trough therein 217 for holding the electrically low conducting food (in this case shown, a hamburger bun) and having an internal surface shaped to fixedly hold the food product when the container or shell or enclosure is in a closed position prior to, during and subsequent to the electrical resistance cooking operation. The electrical contacts 236 and 236' need not be exactly diametrically opposite one another but may be somewhat closer together and efficient heating of the electrically high conducting food substance will still take place.

FIG. 18 is a front perspective view of the invention showing the packaged food product with the enclosure therefor in an open position wherein the enclosure 217' is holding an electrically low conducting food 179 and 179' (in this case, a hamburger bun) which is enveloping an electrically high conducting food 178 (in this case, a hamburger.

FIG. 19 is a front perspective view of our invention showing the packaged food product consisting of the electrically low conducting food (such as a hamburger bun) enveloping the electrically high conducting food (such as a hamburger) totally enclosed within a hollow thermally and electrically insulating container 301' and 301" with electrical contacts 236 and 236' protruding therefrom at 247 and 247' (which electrical contacts are caused by the design of the container or shell or enclosure to be in intimate contact with the hamburger). The electrical contacts 236 and 236' and the surface of the hamburger in contact with the electrical contacts have therebetween a composition at 199 of FIG. 20 comprising a gel such as agar and an ionized species such as salt. The electrical contacts 236 and 236' are connected to a source of electrical energy during the cooking operation (not shown).

FIG. 20 is an enlarged cross-sectional view taken along line 20—20 of FIG. 19 showing a portion of the electrically low conducting food 179 and 179' enveloping the electrically high conducting food 178 (in this case, a hamburger) enclosed within a container 301' and 301", shell or enclosure (which container, shell or enclosure is in a closed position). The electrically high conducting food is shown being cooked using the electrical contacts 236 (e.g., aluminum foil) which extend outwardly from the container, or shell or enclosure at 247 and which are attached to the terminals of an electrical energy source (not shown). In common contact with the electrically high conducting food 178 (in this case, a hamburger) and the electrical contacts 236 is a composition 199 comprising a gel such as agar and an ionized species such as sodium chloride. In this case, the composition of the gel and an ionized species is coated onto and absorbed into the interstices of the surface of the hamburger.

FIG. 21 is an enlarged cross-section view of perforated aluminum foil 435 having coated on both sides thereof a composition 495 comprising a gel such as agar and an ionized species such as sodium chloride. The perforated aluminum foil bearing the said composition acts as an electrical contact which will conduct electrical current from an electrical energy source into the energy source into the electrically high conducting food substance.

FIG. 22 shows a different container, shell or enclosure 401 of our invention (produced by means of thermoforming or vacuum-forming) for the packaged food product of our invention including locking means 410 for holding together the upper 401' and lower 401" sections of the container.

Figure 11:
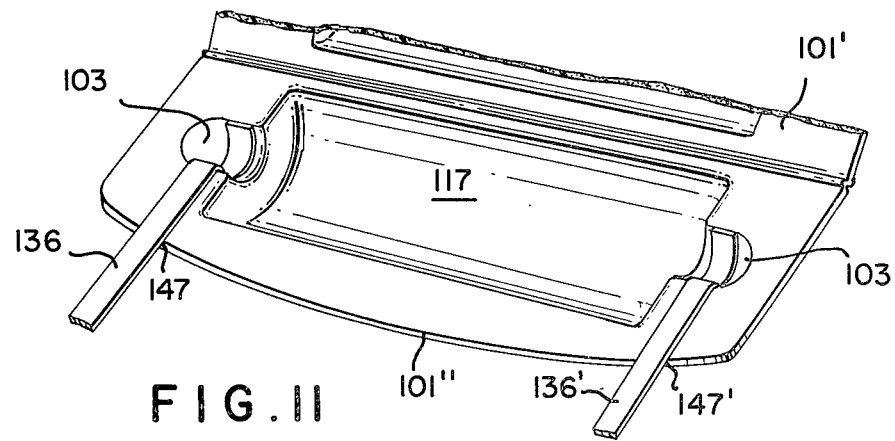
Figure 12:
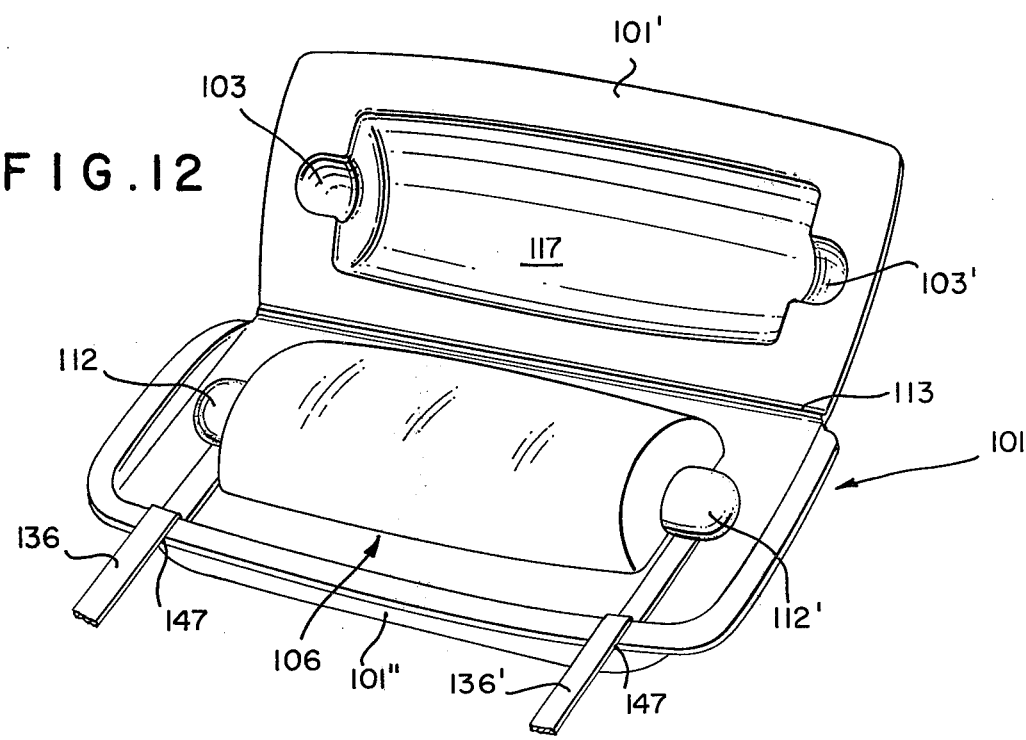
Figure 29:
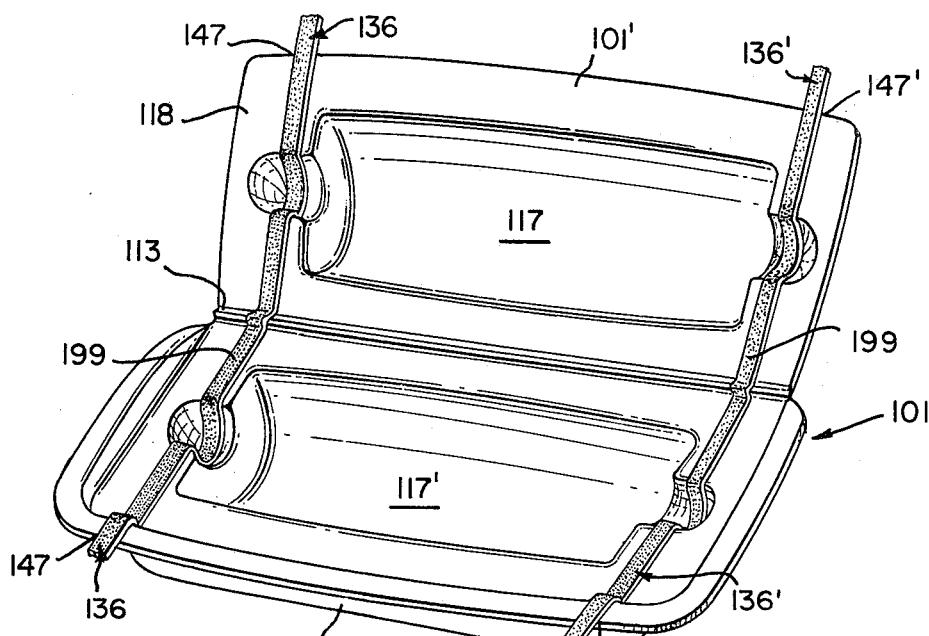

FIG. 29 is a front perspective view of that aspect of our invention which constitutes the enclosure portion 101' and 101" of the packaged food product showing a variation of the enclosure of FIG. 11 in an open position wherein the electrical contacts 136 and 136' located at substantially diametrically opposite ends of the container (intended to be in intimate contact with the ends 211 and 211' of the electrically high conducting food when the container is in a closed position) are two metal ribbons 136 and 136' extending continuously across the inner surface 118 of each end of each portion of said enclosure.

Figure 30:
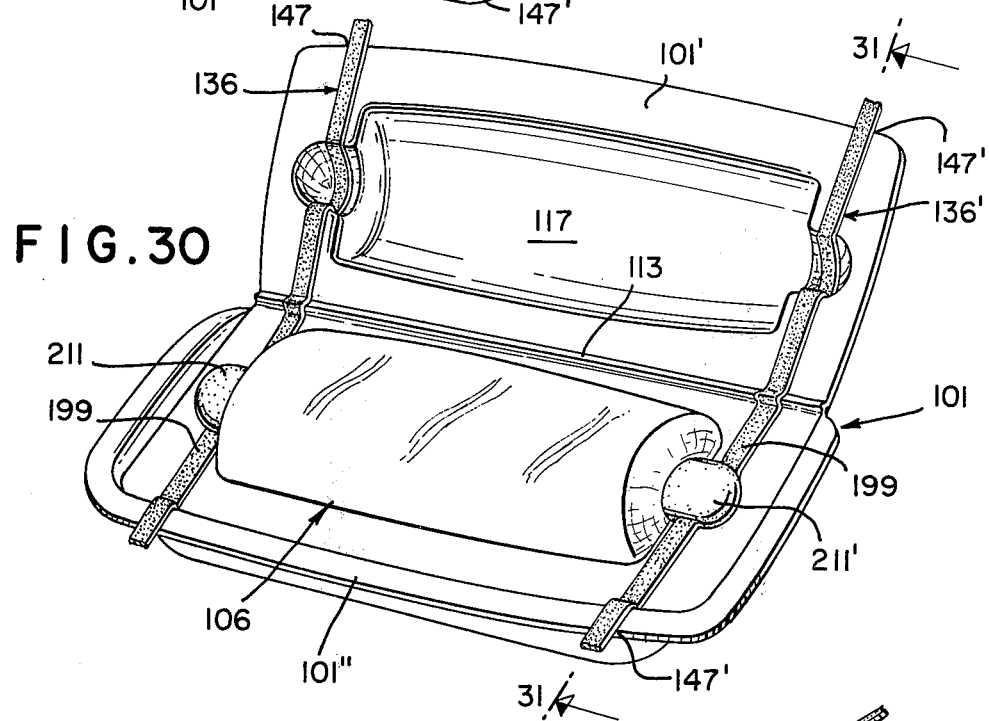

FIG. 30 is a front perspective view of the container shown in FIG. 29 with a low conducting food 106 (a frankfurter bun) holding a high conducting food 109 (a frankfurter) located in the container.

Figure 31:
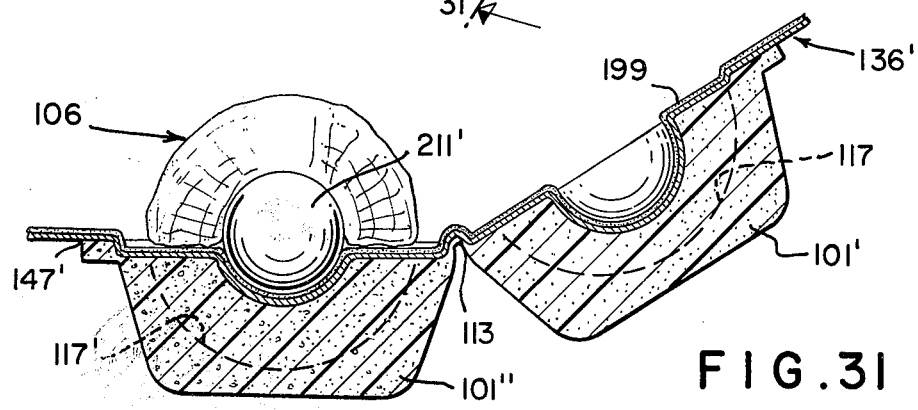

FIG. 31 represents a cross-sectional view taken along lines 31—31 of FIG. 30 showing the composition 199 comprising a gel such as agar and an ionized species such as sodium chloride coated on the electrical contact 136'.

DESCRIPTION OF THE PREFERRED EMBODIMENT

The utilization of the composition of our invention which comprises an ionized species such as sodium chloride, potassium chloride, ammonium chloride, sodium iodide, potassium iodide, magnesium chloride, sodium glutamate, potassium glutamate, sodium alginate, potassium alginate, ammonium alginate, magnesium alginate, calcium alginate, sodium bicarbonate, potassium bicarbonate, magnesium bicarbonate, calcium bicarbonate, sodium nitrate, potassium nitrate, sodium nitrite, and potassium nitrite and a gel such as agar, xanthan gum, tragacanth, guar gum, gum arabic and algin gum as well as water wherein:

i. The weight of water is initially 86 up to 99.3 weight percent;

ii. The weight percent of gel is initially 0.5% up to 4.0% by weight; and iii. The weight percent of edible ionized species is initially from 0.2% up to 10.0% by weight is illustrated at locations 195, 196 and 199 in FIGS. 4,5,6,20,27,28 and 31. The composition may be coated onto electrical contacts 134, 135, 136 or 236 or the composition may be coated onto an electrically high conducting food substance where the electrical contacts are to contact the electrically high conducting food substance 108, (pizza topping), 109 (frankfurter) and 178 (hamburger). Alternatively, the composition of our invention may be coated both onto the electrical contact and onto the electrically high conducting food substance where the electrical contact is in intimate contact with the electrically high conducting food substance.

Figure 4:
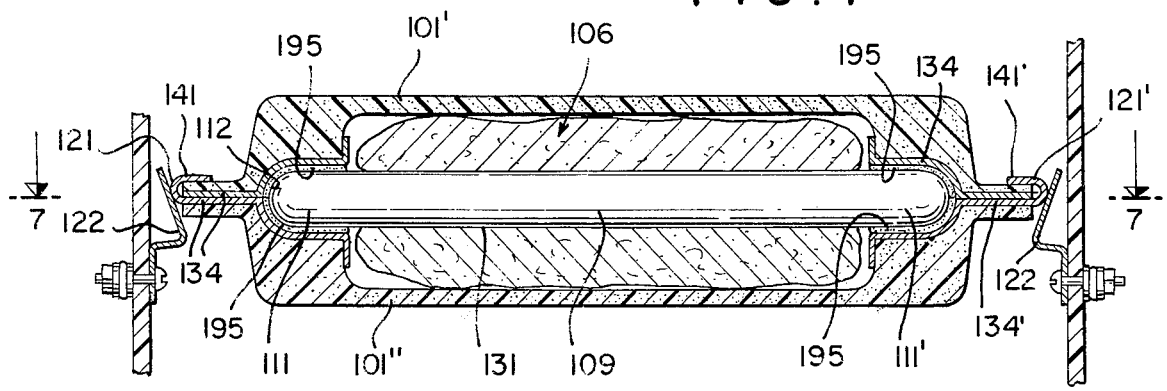
Figure 19:
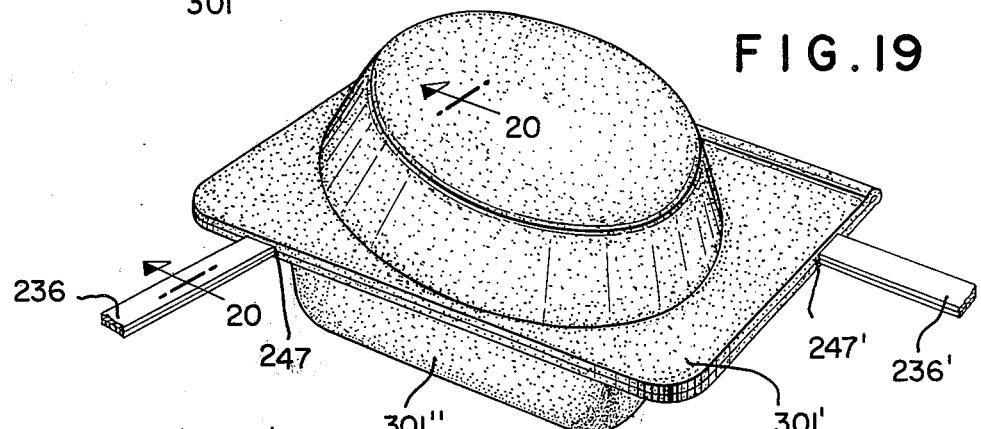
Figure 20:
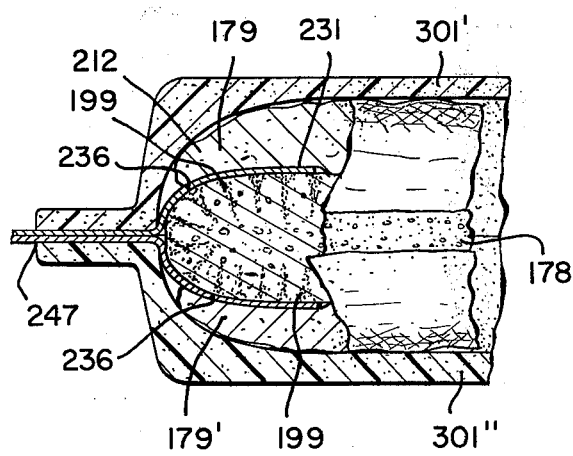
Figure 21:
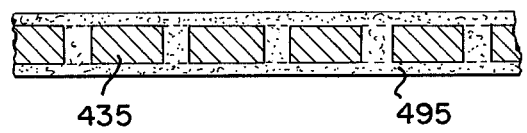
Figure 22:
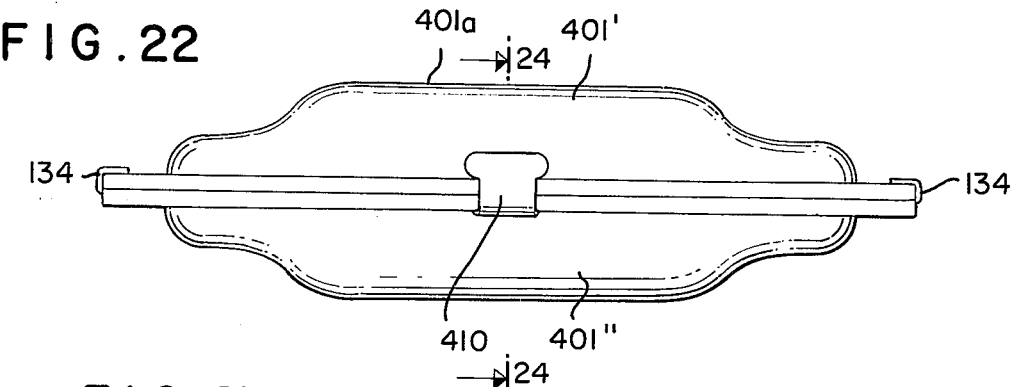
Figure 23:
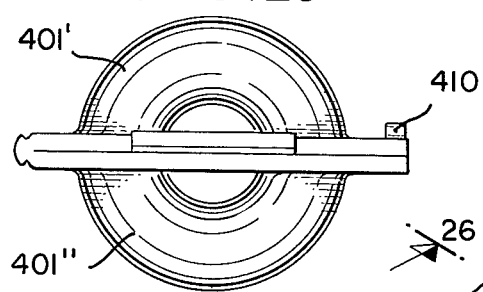
FIG. 23 is a side view taken along lines 23—23 of FIG. 22.
Figure 24:
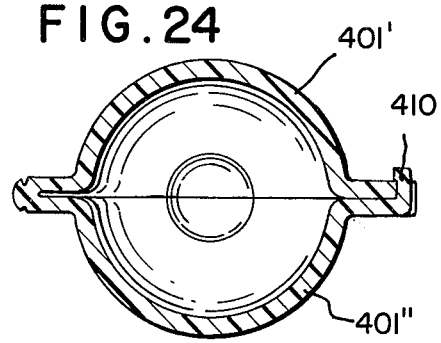
FIG. 24 represents a cross-sectional view taken along lines 24—24 of FIG. 22.

The containerized bare food product of our invention is specifically illustrated in the drawings as comprising, firstly, an electrically low conducting food substance such as a frankfurter bun 106 or pizza dough 114 or a hamburger bun 179; and an electrically high conducting food substance such as a frankfurter 109 disposed in proximate contact at 131 (as shown in FIG. 4) with the low conducting food substance, or such a hamburger 178 disposed in proximate contact at 231 (as shown in FIG. 20) with the hamburger bun said high conducting food having an electrical resistivity of from 1 up to 50 ohm inches over a temperature range of from 30°F up to 250°F and having substantially diametrically opposite ends, e.g., in the case of the hamburger 211 and 211', in the case of the pizza topping 150 and 150' and the case of the frankfurter 111 and 111'. The substantially diametrically opposite ends have substantially solid surfaces 112 and 112' in the case of the frankfurter and 212 in the case of the frankfurter and 212 in the case of the hamburger. At least two electrical contacts 134 and 134' (in the case of the frankfurter) and 236 and 236' (in the case of the hamburger) are located at the substantially diametrically opposite ends of the electrically high conducting food substance in intimate contact with the electrically high conducting food substance such that an electrical current can easily pass from the contact to the electrically high conducting food substance without undergoing a high voltage drop. The composition, as stated above, comprising an edible gel and an edible ionic species is positioned, e.g., at 195 in the case of the frankfurter or at 199 in the case of the hamburger to make intimate contact between the electrically high conducting food substance, e.g., 178 in the case of the hamburger and the two electrical contacts, e.g., 236 and 236' in the case of the hamburger. The electrical contacts extend outwardly beyond the low conducting food (e.g., at 247 and 247' in FIG. 19).

Figure 1:
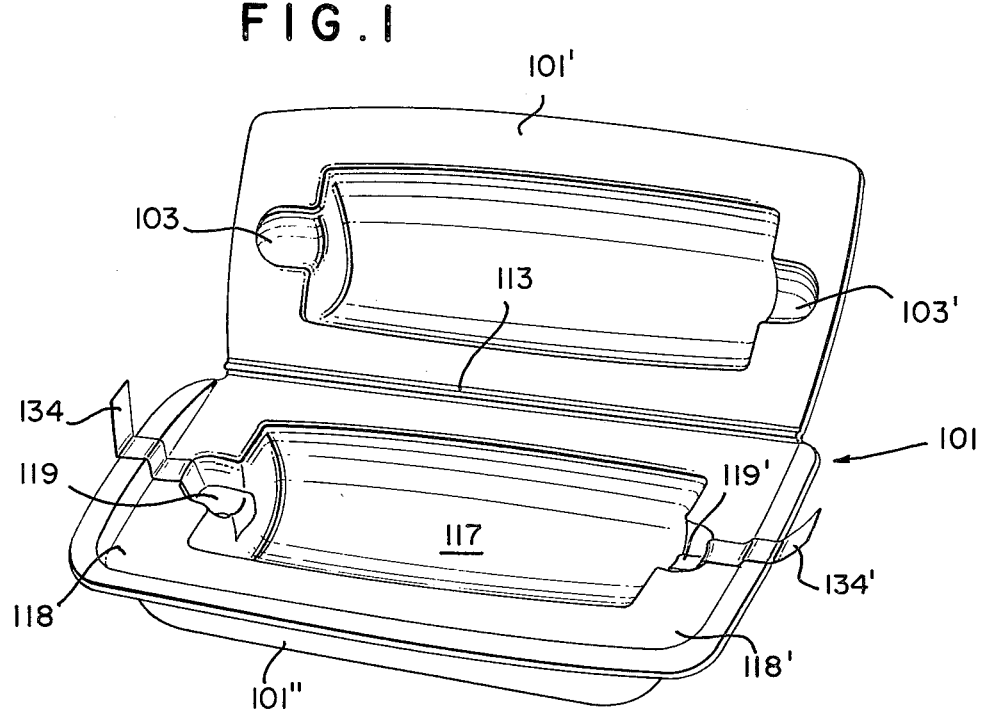
Figure 2:
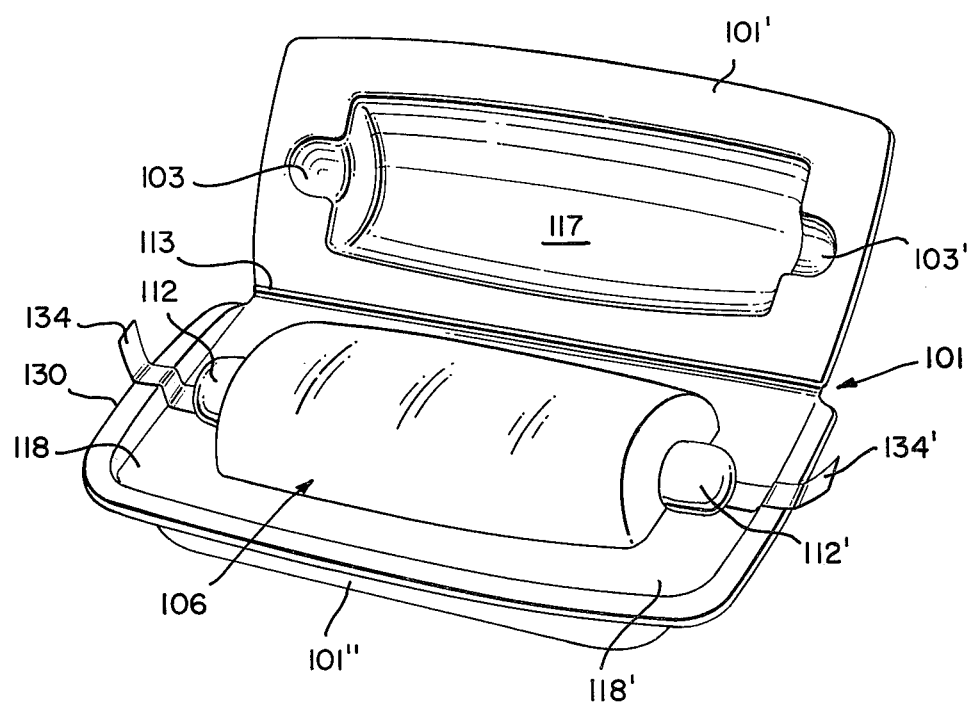
Figure 3:
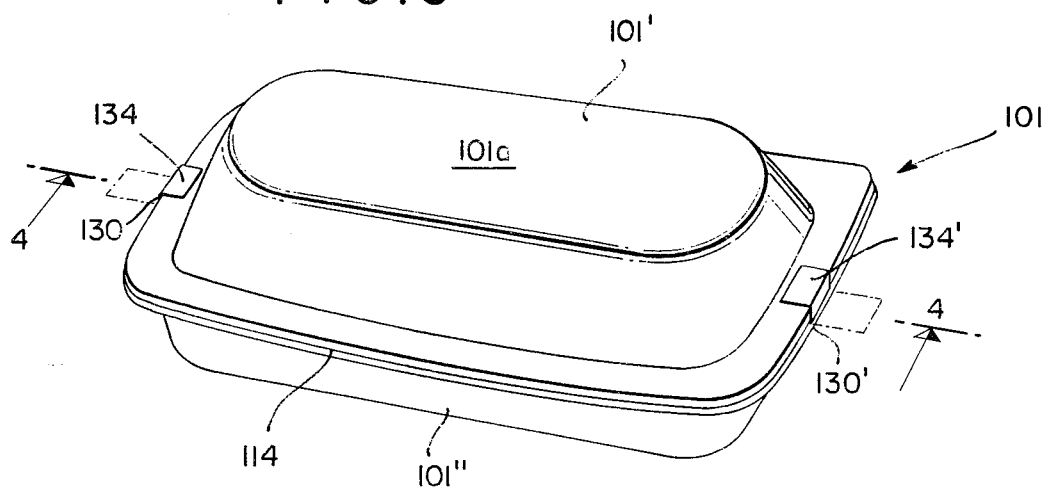
Figure 13:
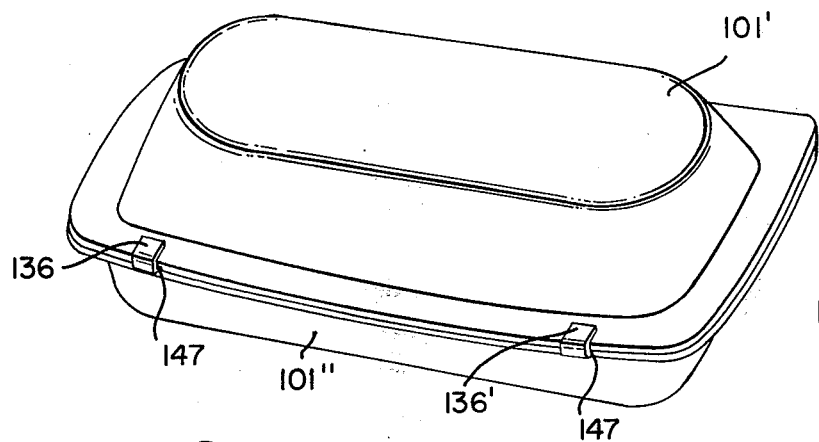
Figure 18:
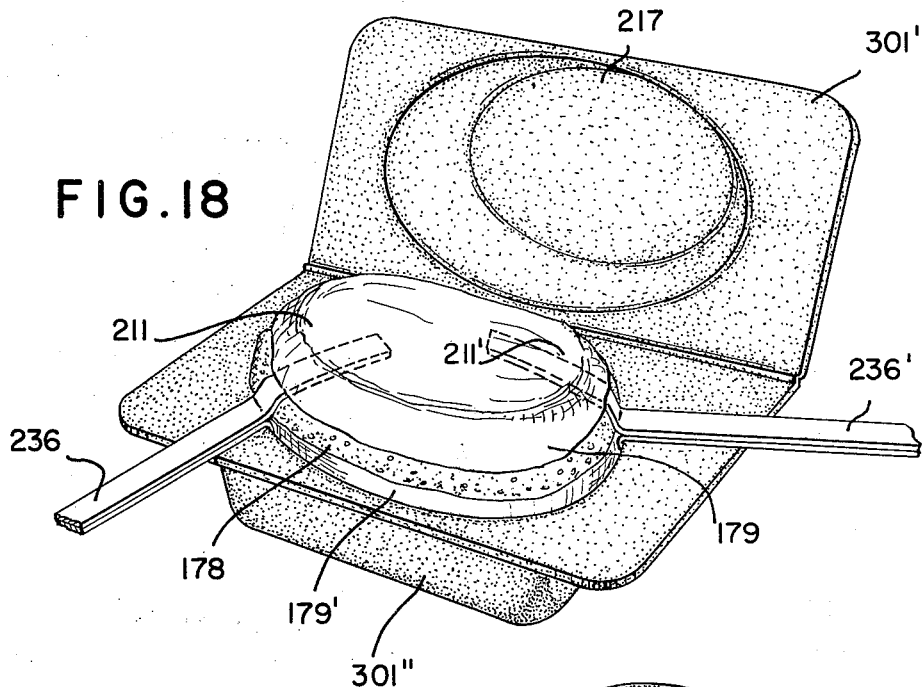

Enclosing the electrically low conducting food is a hollow thermally and electrically insulating substantially moisture impervious enclosure or shell or container (e.g., 101' and 101'') fabricated from, for example, styrofoam having a thickness of fabricated from, for example, styrofoam having a thickness of from 3/32inch up to /inch and a thermal conductivity range over a mean temperature of from 60°F up to 100°F of from 0.2 up to 0.3 BTU/hour-sq. ft. - (°F/inch) the enclosure or shell or container being capable of existing in a closed position shown in FIGS. 3, 13 and 19 and in an open position shown in FIGS. 1, 2, 11, 12, 14, 15, 16, 17, 18 and 22. The outer surfaces 101a (FIG. 1) and 401a (FIG. 22) of the container are so designed as to render said container conveniently adaptable for use in conjunction with an electrical resistance cooking apparatus such as an automatic vending machine as described in U.S. Pat. No. 3,548,738 and 3,651,752. The said container 101 or shell or enclosure is constructed of two sections 101' and 101'' having substantially conterminous edges with section 101' articulating section 101''. In fact, section 101' may be so designed as to be hinged at 113 with section 101'' and/or may interlock at 114 (see FIG. 3) with section 101''. At least one of sections 101' or 101'' has an internal surface 117 designed to fixedly hold the electrically low conducting food substance which is enveloping the electrically high conducting food substance at least at the substantially diametrically opposite ends of the food substance when the container is in a closed position shown by FIGS. 3 and 13. At least one of the container sections 101' or 101'' has substantially diametrically opposite ends 118 and 118' which has internal surfaces 119 and 119' which are co-extensive with the external surfaces of the substantially diametrically opposite ends of the high conducting food portions 111 and 111'. Electrical conducting means such as strips of aluminum foil having a thickness of approximately 0.2 ml, 134 and 134', extend outwardly from the container 101 at 130 and 130' (the ends of the container) or car extend outwardly from container 101 container at 147 or 147' (see FIG. 12) or from the corners of the container (in the case of the hamburger shown in FIG. 19) at 247 and 247'. The electrical conducting means have electrical conducting ends 121 and 121' shown in FIGS. 4, 8 and 9 external to the container or enclosure which ends are designed to make electrical contact with the terminals 122 and 122' of the electrical energy source when the container is in a closed position as illustrated by FIG. 3.

Figure 5:
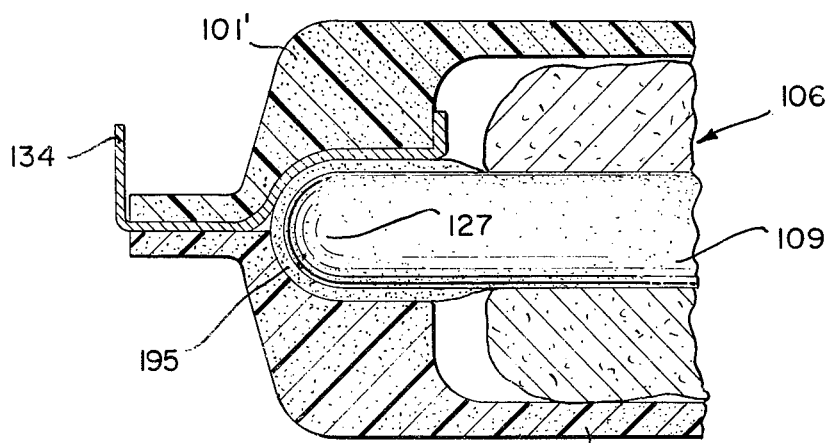
Figure 15:
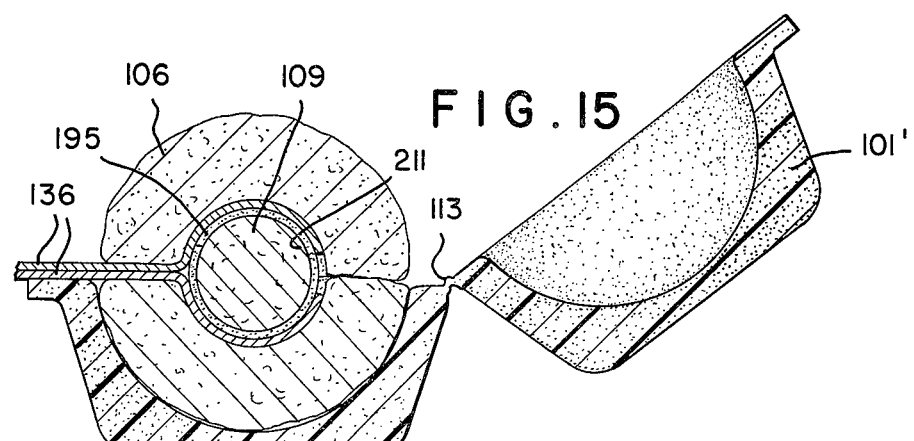
Figure 16:
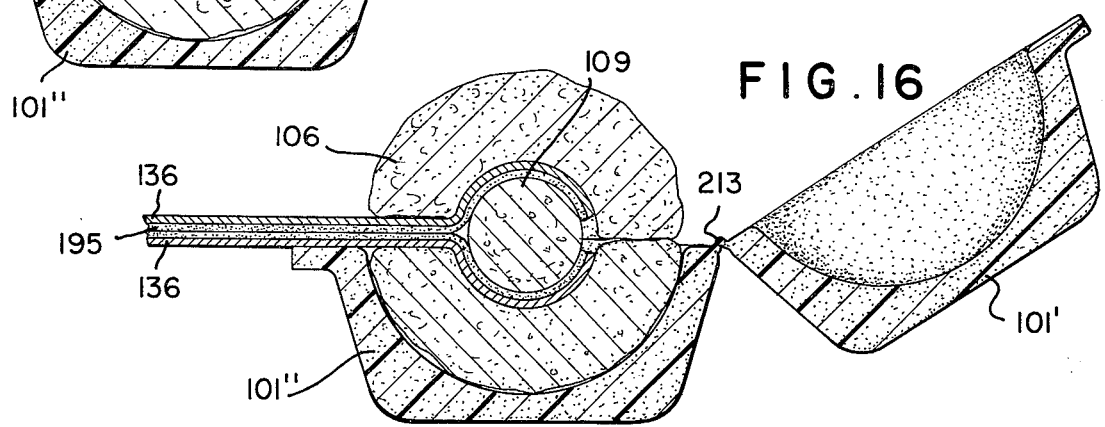
Figure 17:
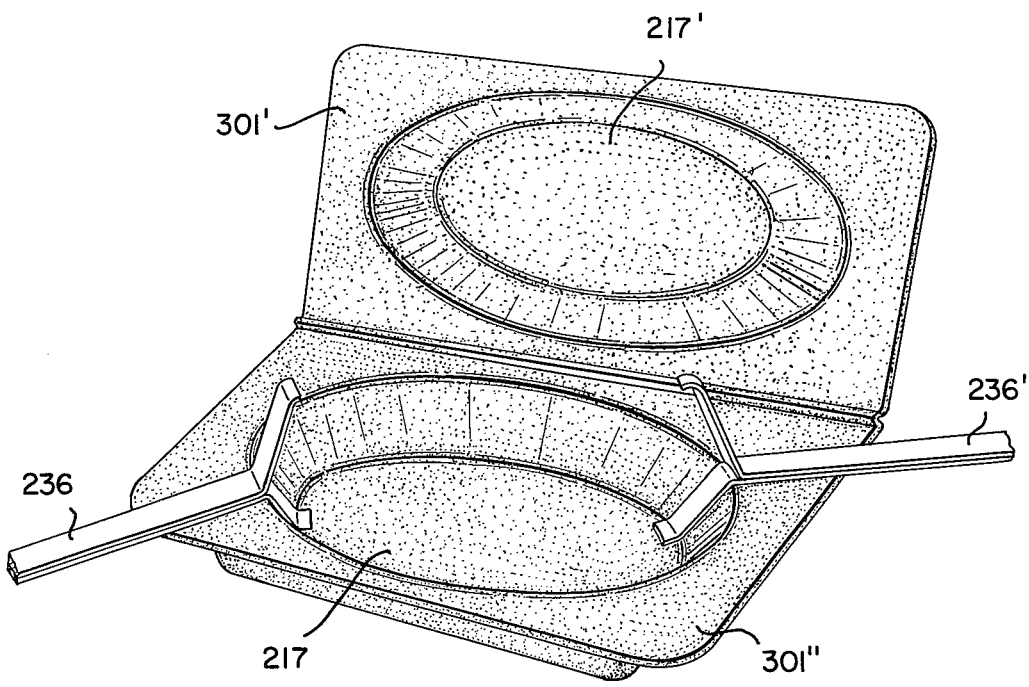

In common intimate contact with at least two portions (having a substantial degree of separation therebetween) of at least one of the external surfaces of the high conducting food are:

1. an electrically high conducting composition comprising a gel and an edible ionic species as illustrated in FIG. 5 at 127 and in FIG. 15 at 109 and in FIG. 20 at 212; and 2. at least two electrical contacts shown as 134 in FIG. 4 and as 136 in FIG. 15, the composition being positioned to make intimate contact between the two electrical contacts and the substantially solid surface of the electrically high conducting food substance at, for example 127 of FIG. 5.

When ready for use in conjunction with an electrical resistance cooking apparatus, the portions of the electrical conducting means such as the aluminum foil external to the walls of the container or shell or enclosure are preferably bent back substantially adjacent to the surfaces of the container or shell or enclosure walls at (141) and (141'), thus enabling effective low-resistance electrical contact to be maintained between the terminals 122 and 122' and the ends 121 and 121'. The presence of the composition 195 comprising the gel and the ionized species prevents arcing when the low resistance electrical contact is maintained between the terminals and the ends 121 and 121'. Portions of the electrical conducting means, 134 and 134' which are on the internal surfaces of the substantially diametrically opposite high conducting food portions 111 and 111' and which are in contact with the internal surfaces of the diametrically opposite ends 118 and 118' of the container or shell or enclosure may be coated with the composition comprising the gel and the ionized species at 195. By the same token, portions of the electrical conducting means 134 and 134' which are on the internal surfaces of the diametrically opposite ends 118 and 118' of the container or shell or enclosure will be in intimate electrical contact with the external surfaces 112 and 112' of the two diametrically opposite high conducting food portions 111 and 111' when the container is in a closed position as illustrated in FIG. 3 or FIG. 19.

Figure 9:
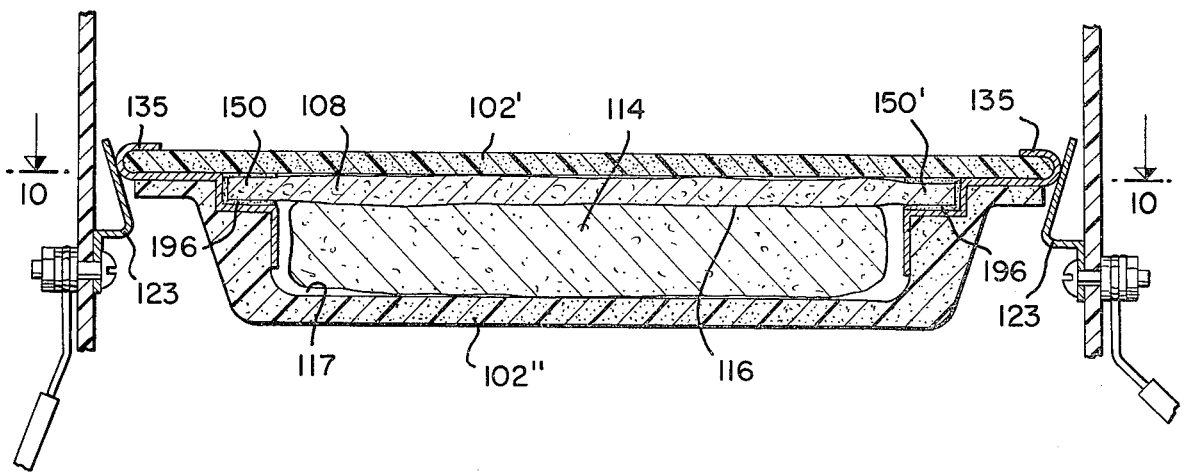
Figure 14:
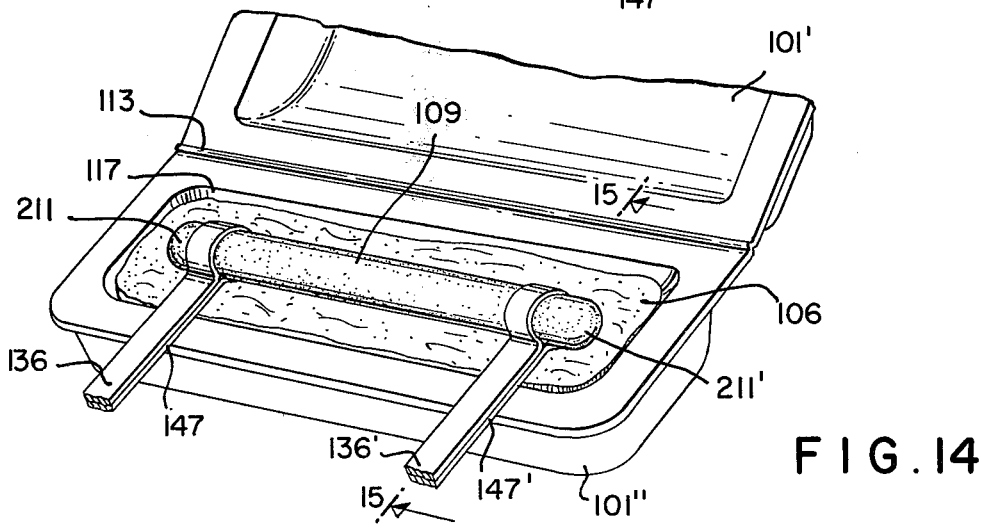

The electrically high conducting food substance such as a frankfurter or hamburger may be disposed substantially within the low conducting food substance as illustrated in FIGS. 4, 14 and 18. Alternatively, the electrically high conducting food substance may be disposed in contact with but one surface of the low conducting food as in the case of a pizza slice as illustrated in FIG. 9.

The edges of the enclosure or shell or containers are substantially conterminous and may be interrupted at 147 and 147' or at 247 and 247' at the proximate regions 111 and 111' or 211 and 211' of the substantially diametrically opposite high conducting food portions, such that discrete minute container openings exist at these proximate regions. The preferred ratio of the surface area of the contacted high conducting food substance (that is with an electrical contact) to the surface area of non-contacted high conducting food substance is from 1:15 up to 1:4. The electrically high conducting food, 109 in the case of the frankfurter may also be thermally high conducting.

Figure 25:
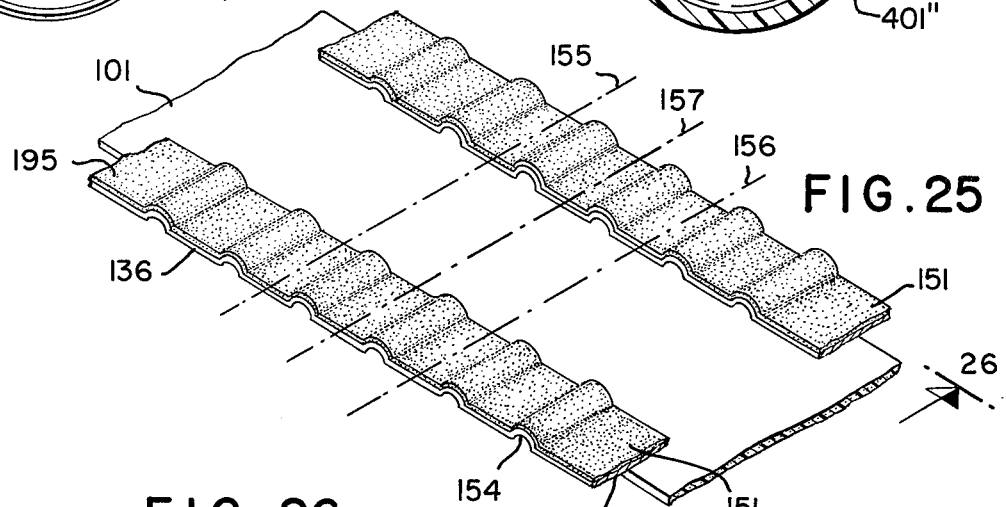
FIG. 25 represents a front perspective view of an uncut polymer sheet having adhered thereto metal foil strips 136, having coated on said metal foil strips a composition 195 comprising a gel such as agar and ionized species such as sodium chloride, prior to thermoforming, for the purpose of producing a thermoformed or vacuum-formed container, shell or enclosure of FIG. 22.
Figure 26:
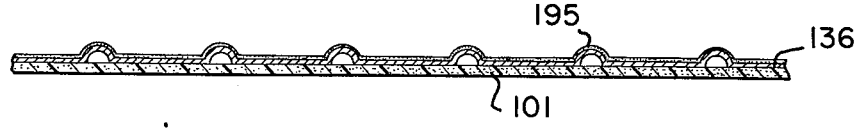
FIG. 26 represents a schematic cross-sectional view taken along lines 26—26 of FIG. 25.
Figure 27:
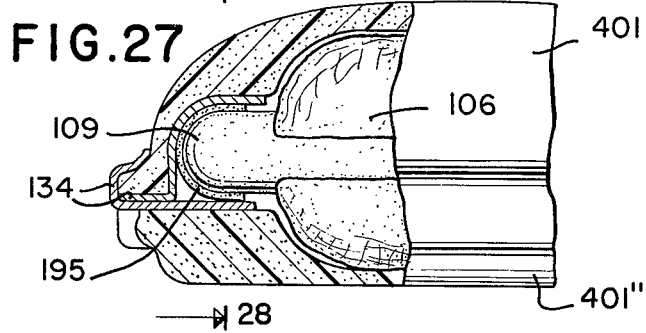
FIG. 27 is a side view of a partially cut-away packaged food product comprising our invention wherein the container, shell or enclosure thereof is produced by thermoforming.
Figure 28:
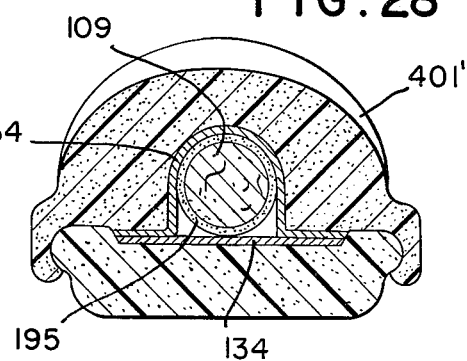
FIG. 28 is a cross-sectional view taken along line 28—28 of FIG. 27.

The container itself may be produced by molding or by thermoforming. As illustrated in FIG. 25 the electrically conducting foil 136 may be firstly coated with the edible composition 195 (whose presence prevents arcing during the electrical resistance cooking operation) comprising a gel and an ionized species. The thus coated electrically conducting foil 136 is then attached to the flat polymeric sheet 101 in strips 151 prior to thermoforming in such a way that an excess of foil beyond the planar shape of the plastic sheet at 153 is present permitting the foil to follow the contours of the shaped plastic at regions 154 without tearing. After deep drawing the plastic sheet, the container forms are cut along lines 155 and 156 and folded along line 157. The coating of the metal foil with the composition comprising the gel and the ionized species obivates the necessity of coating the electrically high conducting food substance in order to cause the prevention of arcing during the electrical resistance cooking operation. However, the fact that the electrically conducting foil 136 is precoated with the composition 195 comprising the gel and the ionized species is not to mean that the electrically high conducting food substance should not be coated with the ionized species and the gel composition too. Indeed, an operable embodiment of our invention is to coat both the electrically high conducting food substance at the point of contact of the electrical contacts and the electrical foil with the gel and the ionized species composition.

The following examples serve to further illustrate additional embodiments of our invention concerning the composition of the gel and ionized species as it is now preferred to practice it. It will be understood that these examples are illustrative and that our invention is to be considered restricted thereto only as indicated in the appended claims.

EXAMPLE I

A six inch by three-quarter inch beef frankfurter is coated at each end to the extent of one inch with a warm aqueous solution of 2% agar and 4% sodium chloride. After setting of the gel by cooling, the frankfurter is placed in a bun and the combination frankfurter and bun is placed in a container having electrical contacts attached thereto and connected to a source of electrical energy as illustrated in FIG. 4. Over a period of 18 seconds, a primary voltage of 115 volts stepped up to 340 volts is applied to the electrical contacts from the electrical energy source which results in a flow of 1.2 up to 3.4 amperes. (To achieve equivalent results, a primary voltage of 110, 220 or 440 volts may be transformed to an applied voltage in the range of 300–400 volts.) The frankfurter roll and frankfurter resulting from the aforementioned treatment is described as "very hot, steaming and slightly split". No arcing took place during the heating operation.

EXAMPLES II — XXIX

The same procedure as Example I is followed in the following examples set forth in the following table. Varied are the gel ionized species composition and the electrical energy contact time and voltage.

| Example | Gel-Ionized Species Combination | Description of Electrical Energy | Result of Electrical Resistance Cooking |
|---|---|---|---|
| II | 2% agar & 5% sodium chloride | Primary voltage of 115 volts stepped up to 335 volts, applied over a period of 12 seconds/1.5–3.2 amperes. | Very hot, steaming. |
| III | 2% agar & 5% sodium chloride | Primary voltage of 115 volts stepped up to 340 volts, applied over a period of 8 seconds/ 1.4–3.2 amperes. | Hot, not steaming. |
| IV | 2% agar & 5% sodium chloride | Primary voltage of 115 volts stepped | Hot, just starting to |

-continued

| Example | Gel-Ionized Species Combination | Description of Electrical Energy | Result of Electrical Resistance Cooking |
|---|---|---|---|
| | | up to 345 volts, applied over a period of 10 seconds/1.4–3.2 amperes. | steam. |
| V | 2% agar & 5% sodium chloride Agar allowed to set on frankfurter before cooking. | Primary voltage of 115 volts stepped up to 345 volts, applied over a period of 10 seconds/1.4–3.2 amperes. | Hot, steaming. |
| VI | 4% gelatin & 5% sodium chloride | Primary voltage of 115 volts stepped up to 335 volts, applied over a period of 10 seconds/0.8–2.5 amperes. | Frankfurter just warm; arced at end (9 seconds). |
| VII | 4% gelatin & 5% sodium chloride | Primary voltage of 115 volts stepped up to 335 volts, applied over a period of 10 seconds/0.8–2.2 amperes. | Frankfurter just warm; arced at 7 seconds. |
| VIII | 4% gelatin & 5% sodium chloride (Gelatin allowed to dry on hot dog) | Primary voltage of 115 volts stepped up to 340 volts, applied over a period of 10 seconds/0.8–1.2 amperes. | Slight warming; arced at 5 seconds. |
| IX | Gelatin 8% & sodium chloride 5% | Primary voltage of 115 volts stepped up to 345 volts, applied for a period of 10 seconds/1.0–2.6 amperes. | Frankfurter just warm; arcing at 9 seconds. |
| X | Gelatin 8% & sodium chloride 5% | Primary voltage of 115 volts stepped up to 350 volts, applied for a period of 10 seconds/1.2–2.8 amperes. | Cooked, hot frankfurter, no arcing. |
| XI | Gelatin 8% & sodium chloride 5% | Primary voltage of 115 volts stepped up to 335 volts, applied for a period of 10 seconds/1.0–2.6 amperes. | Frankfurter cooked and hot, no arcing. |
| XII | 2% agar & ½% graphite | Primary voltage of 115 volts stepped up to 335 volts, applied for a period of 10 seconds/1.20 amperes. | No cooking (arced at 3 seconds). |
| XIII | Agar 2% & ½% graphite | Primary voltage of 115 volts stepped up to 340 volts, applied for a period of 10 seconds/0.8–2.2 amperes. | Frankfurter slightly warmed but arced at 7 seconds. |
| XIV | Gelatin 12% & sodium chloride 5% | Primary voltage of 115 volts stepped up to 355 volts, applied for a period of 10 seconds/1.2–2.2 amperes. | Frankfurter hot but arced just at the end of the 10-second period. |
| XV | Gelatin 12% & Sodium Chloride 5% | Primary voltage of 115 volts stepped up to 350 volts, applied over a period of 10 seconds/1.2–2.4 amperes. | Frankfurter just warm, arced at 7 ½ seconds. |
| XVI | 2% agar, ½% sodium chloride & ½ % graphite | Primary voltage of 115 volts stepped up to 335 volts, applied over a period of 10 seconds/1–2.8 | Frankfurter hot but arced just at the end of the 10-second period. |

-continued

| Example | Gel-Ionized Species Combination | Description of Electrical Energy | Result of Electrical Resistance Cooking |
|---|---|---|---|
| XVII | Agar 2%, sodium chloride ½%, graphite ½% | Primary voltage of 115 volts stepped up to 340 volts, applied over a period of 10 seconds/1.0–3.1 amperes. | Frankfurter hot and cooked and no arcing took place. |
| XVIII | Gelatin 12%, Sodium Chloride 7 ½% | Primary voltage of 115 volts stepped up to 340 volts, applied over a period of 10 seconds/1.2–2.3 amperes. | Frankfurter warmed but arcing at 6 seconds. |
| XIX | Agar 2% and sodium chloride 5% | Primary voltage of 115 volts stepped up to 345 volts, applied over a period of 10 seconds, 1.4–3.2 amperes. | Frankfurter very hot and steaming. |
| XX | Agar 2%, sodium chloride 5% | Primary voltage of 115 volts stepped up to 345 volts, applied over a period of 12 seconds/1.4–3.4 amperes. | Frankfurter very hot and shivelled. |
| XXI | Agar 2%, sodium chloride 5% | Primary voltage of 115 volts stepped up to 340 volts, applied over a period of 12 seconds/1.4–2.8 amperes. (Configuration according to FIG. 2 rather than FIG. 14) | Frankfurter hot and cooked. |
| XXII (Control) | Sodium Chloride 5% | Primary voltage of 115 volts stepped up to 355 volts, applied over a period of 12 seconds/1.4–2.7 amperes. (Aluminum foil in container according to FIG. 2) | Arcing at 3 seconds; no cooking. |
| XXIII | Gelatin 2%, sodium chloride 5% | Primary voltage of 115 volts stepped up to 350 volts, applied over a period of 12 seconds/1.2–2.2 amperes. (Aluminum foil in container according to FIG. 2) | Frankfurter just warm; arcing at 9 seconds. |
| XXIV | Agar 2%, sodium chloride 5% | Primary voltage of 115 volts stepped up to 355 volts, applied over a period of 10 seconds/1.8–3.3 amperes. (Configuration according to FIG. 2 except 4 aluminum strips 2 in each cavity). | Frankfurter extremely hot. |
| XXV | 2% agar, 5% sodium chloride | Primary voltage of 115 volts stepped up to 355 volts, applied over a period of 10 seconds/1.7–3.1 amperes. (Configuration according to FIG. 2 except 4 aluminum strips 2 in each cavity). | Frankfurter very hot. |
| XXVI (Control) | 5% Sodium Chloride | Primary voltage of 115 volts stepped up to 340 volts, applied over a period of 10 seconds/1.2–2.1 amperes. (Config- | Arcing at 4 seconds. |

| Example | Gel-Ionized Species Combination | Description of Electrical Energy | Result of Electrical Resistance Cooking |
|---|---|---|---|
| XXVII | Agar 2%, sodium chloride 5% | uration according to FIG. 2) Primary voltage of 115 volts stepped up to 345 volts, applied over a period of 10 seconds/1.8–3.4 amperes. (Configuration according to FIG. 14) | Frankfurter very hot. |
| XXVIII | 2% Agar, 5% sodium chloride | Primary voltage of 115 volts stepped up to 345 volts, applied over a period of 8 seconds/1.6–3.1 amperes. (Configuration as in FIG. 14). | Frankfurter hot. |
| XXIX (Control) | 2% Sodium Chloride | Primary voltage of 115 volts stepped up to 350 volts, applied over a period of 8 seconds/0.6–2.8 amperes. (Configuration as in FIG. 14). | Arcing at 8 seconds, no cooking. |

EXAMPLES XXX – LVI

A six inch by three-quarter inch all beef frankfurter is coated similarly to Example I and is placed in a frankfurter roll which extends beyond the diametrically opposite ends of said frankfurter. The frankfurter in the roll is placed in a container desinged as in FIGS. 22, 23, 24 or FIGS. 27 and 28. The container is produced from thermoformed polyvinyl chloride. The following table sets forth the electrical energy variables as well as the gel-ionized species composition variables upon which the efficiency of cooking of the packaged food product of our invention is dependent:

| Example | Gel-Ionized Species Combination | Description of Electrical Energy | Result of Electrical Resistance Cooking |
|---|---|---|---|
| XXX | 5% sodium chloride, 2½% gum tragacanth | Primary voltage of 115 volts stepped up to 340 volts, applied over a period of 10 seconds/1.2–3.1 amperes. | Frankfurter very hot. |
| XXXI | 5% sodium chloride, 2½% gum tragacanth | Primary voltage of 115 volts stepped up to 345 volts, applied over a period of 10 seconds/1.2–3.3 amperes. | Frankfurter very hot. |
| XXXII | 5% sodium chloride; 2½% gum tragacanth (solution allowed to "set" on frankfurter) | Primary voltage of 115 volts stepped up to 360 volts, applied over a period of 10 seconds/1.8–4.0 amperes. | Frankfurter very, very hot. |
| XXXIII | 5% sodium bicarbonate; 2½% gum tragacanth | Primary voltage of 115 volts stepped up to 345 volts, applied for a period of 10 seconds/1.4–2.9 amperes. | Frankfurter cooked but not as hot as in Examples XXX or XXXI. |
| XXXIV | 5% sodium bicarbonate; 2½% gum tragacanth | Primary voltage of 115 volts stepped up to 350 volts, applied for a period of 10 seconds/1.4–3.0 amperes. (Composition allowed to set up on hot dog before cooking). | Frankfurter hot. |
| XXXV | 5% sodium bicarbonate; 2½% | Primary voltage of 115 volts stepped | Frankfurter warm but not |

-continued

| Example | Gel-Ionized Species Combination | Description of Electrical Energy | Result of Electrical Resistance Cooking |
|---|---|---|---|
| | gum tragacanth | up to 350 volts, applied for a period of 10 seconds/1.2–2.5 amperes. (Configuration whereby frankfurter at one end of bun was outside of roll and the other end of bun was within roll). | hot. |
| XXXVI | 5% sodium chloride, 2½% gum tragacanth | Primary voltage of 115 volts stepped up to 360 volts, applied for 10 seconds/1.8–3.4 amperes. (Composition allowed to set up on frankfurter before commencing cooking). | Frankfurter hot. |
| XXXVII | ½% carboxy methyl cellulose; 5% sodium chloride | Primary voltage of 115 volts stepped up to 365 volts, applied for 10 seconds/1.6–3.6 amperes. | Frankfurter hot. |
| XXXVIII | ½% carboxy methyl cellulose, 5% sodium chloride | Primary voltage of 115 volts stepped up to 350 volts, applied for a period of 10 seconds/1.4–2.6 amperes. | Frankfurter undercooked and warm. |
| XXXIX | ½% carboxy methyl cellulose, 5% sodium chloride | Primary voltage of 115 volts stepped up to 355 volts, applied for a period of 10 seconds/1.5–3.0 amperes. | Frankfurter and bun hot. |
| XL | ½% carboxy methyl cellulose, 5% sodium chloride | Primary voltage of 115 volts stepped up to 360 volts, applied for two 10 second periods/ first period 1.5–3.3 amperes, second period 2.6–3.4 amperes. | Frankfurter and bun very, very hot. |
| XLI | 10% sodium chloride, 2 ½% gum tragacanth | Primary voltage of 115 volts stepped up to 340 volts, applied for a period of 10 seconds/1.5–3.0 amperes. | Frankfurter and bun hot. |
| XLII | 2 ½% gum tragacanth, 10% sodium chloride | Primary voltage of 115 volts stepped up to 345 volts, applied for a period of 10 seconds/1.6–3.4 amperes. (Solution set up on frankfurter prior to electrical resistance cooking). | Frankfurter and bun hot. |
| XLIII | 2½% gum tragacanth, 10% sodium chloride | Primary voltage of 115 volts stepped up to 345 volts, applied for a period of 10 seconds/2.0–3.2 amperes. (Entire hot dog coated with composition). | Arcing occurred at 3.2 amps, not serviceable. |
| XLIV | 1% xanthan gum, 5% sodium chloride | Primary voltage of 115 volts stepped up to 340 volts, applied for a period of 10 seconds/1.4–2.5 amperes. (Extra long (8 inches) hot dog). | Frankfurter warm. |
| XLV | 1% xanthan gum, 5% sodium chloride | Primary voltage of 115 volts stepped | Frankfurter hot. |

-continued

| Example | Gel-Ionized Species Combination | Description of Electrical Energy | Result of Electrical Resistance Cooking |
|---------|--------------------------------|----------------------------------|------------------------------------------|
| | | up to 350 volts, applied for two 10 second periods/ first period 1.6–3.2 amperes; second period 3.2–3.8–2.6 amperes. | |
| XLVI | 2½% gum tragacanth, no ionized species | Primary voltage of 115 volts stepped up to 335 volts, applied for a period of 10 seconds/1.4–2.7 amperes. | Frankfurter and bun hot. |
| XLVII | 2½% gum tragacanth, no ionized species | Primary voltage of 115 volts stepped up to 335 volts, applied for a period of 10 seconds/1.4–3.2 amperes. | Frankfurter and bun hot. |
| XLVIII | 2½% gum tragacanth, 1% sodium chloride | Primary voltage of 115 volts stepped up to 340 volts, applied for a period of 10 seconds/1.4–2.9 amperes. | Frankfurter and bun hot. |
| XLIX | 2½% gum tragacanth, 1% sodium chloride | Primary voltage of 115 volts stepped up to 340 volts, applied for two 10 second periods/ first period 1.4–2.8 amperes; second period 3.0–2.8 amperes. | Frankfurter and bun hot. |
| L (Control) | ½% carboxy methyl cellulose, no ionized species | Primary voltage of 115 volts stepped up to 345 volts, applied for a period of 10 seconds/1.4–2.5 amperes. | Frankfurter just warm. |
| LI | ½% carboxy methyl cellulose, no ionized species | Primary voltage of 115 volts stepped up to 340 volts, applied for a period of 10 seconds/1.4–2.4 amperes. | Arced at end of 10-second period; not servicable. |
| LII | ½% carboxy methyl cellulose, 1% sodium chloride | Primary voltage of 115 volts stepped up to 340 volts, applied for two 10 second periods/ first period 1.4–2.5 amperes, second period 2.5 amperes. | Arcing at end of second period, not servicable. |
| LIII | ½% carboxy methyl cellulose, 3% sodium chloride | Primary voltage of 115 volts stepped up to 350 volts, applied for two 10 second periods/ first period 1.6–2.9 amperes; second period 3.0 amperes. | Arcing at 8 seconds; not serviceable. |
| LIV | 2 ½% gum tragacanth, 10% sodium chloride | Primary voltage of 115 volts stepped up to 355 volts, applied for two 10 second periods/ first period 1.6–3.0 amperes; second period 3.2–3.6 amperes. | Frankfurter and bun very, very hot; no arcing. |
| LV | 2 ½% gum tragacanth, 10% sodium chloride | Primary voltage of 115 volts stepped up to 340 volts, applied for a period of 10 seconds. | Frankfurter cooked well; hot. |

EXAMPLES LVI – LIX

In the following Examples LVI – LIX a hamburger being coated at opposite ends thereof with a coating comprising 2½% gum tragacanth and 1% sodium chloride (the coating covering 20% of the surface area of the hamburger) weighing 4 ounces is placed in a standard hamburger bun and placed in a polyvinyl chloride thermoformed container as illustrated in FIGS. 18, 19 and 20. Over various periods of time, a primary voltage of 115 volts stepped up to 370–400 volts is applied to the electrical contacts from the electrical energy source which results in flows of various quantities of electric current. The electrical energies applied and the results obtained are set forth in the table below:

| Example | Description of Electrical Energy | Result of Electrical Resistance Cooking |
|---|---|---|
| LVI | Primary voltage of 115 volts stepped up to 380 volts, applied for a period of 15 seconds/1.8–4.4 amperes; 3 seconds/4.4–4.0 amperes (total-18 seconds). | Arcing at 18 seconds. |
| LVII | Primary voltage of 115 volts stepped up to 385 volts, applied for a period of 15 seconds/3.2–6.2–6.0 amperes. | Very hot, fully cooked hamburger. |
| LVIII | Primary voltage of 115 volts stepped up to 380 volts, applied for two 12 second periods/ first period 3.2–5.8 amperes; second period 5.8–5.4 amperes. | Very, very hot hamburger but arcing at 4 seconds of second period. |
| LIX | Primary voltage of 115 volts stepped up to 390 volts, applied for a period of 12 seconds/3.0–6.0 amperes. | Very hot, fully cooked hamburger, no arcing. |

EXAMPLES LX AND LXI

Figure 10:
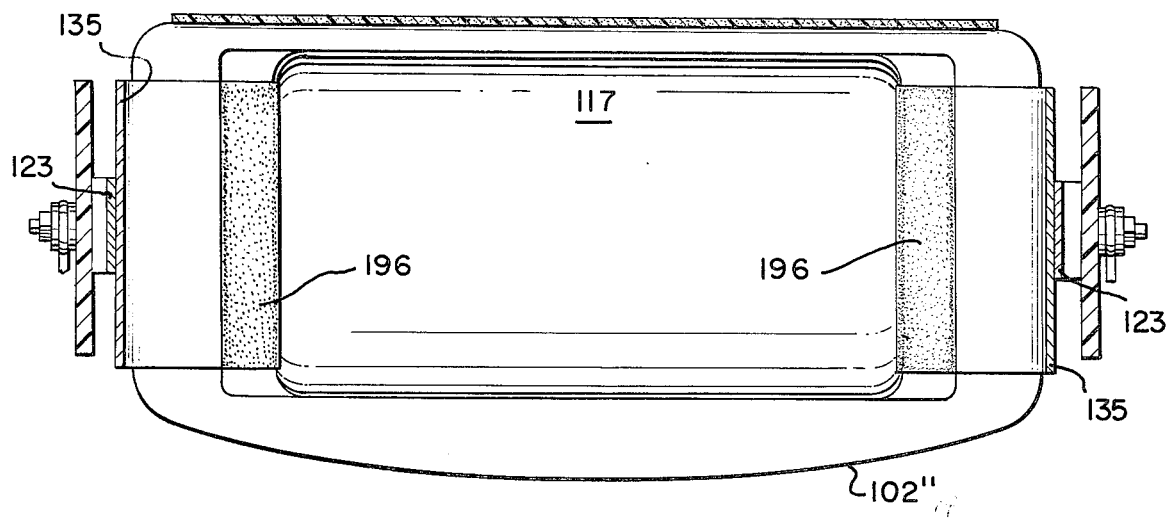

A pizza slice is cooked using the electrical resistance cooking of this invention after coating the ends of the electrically conducting portion with a composition containing 2½% gum tragacanth, 1% sodium chloride and the remainder water. The container used is made of styrofoam and the configuration is in accordance with FIGS. 8, 9 and 10. The following table sets forth the variables for electrical energy, time of electrical energy input and results of experiments:

| Example | Description of Electrical Energy | Result of Electrical Resistance Cooking |
|---|---|---|
| LX | Primary voltage of 115 volts stepped up to 370 volts, applied for two 12 second periods/ 0.1–1.0 amperes for first period; 1.2–2.0 amperes for second period. | Pizza warm and cooked. |
| LXI | Primary voltage of 115 volts stepped up to 375 volts, applied for a period of 18 seconds/0.1–2.0 amperes. | Pizza warm and cooked. |

EXAMPLES LXII – LXIV

The following examples show the cooking of corn beef the diametrically opposite ends of which are coated with a composition comprising 2½% gum tragacanth, 1% sodium chloride, remainder being water. Electrical contacts are applied to the portions of the corn beef which are coated with the gum tragacanth and sodium chloride composition. Two slices of corn beef are placed on a bun and cooked in accordance with FIGS. 8, 9 and 10. The following table sets forth the results obtained when varying electrical energies for varying periods of time are applied to the electrical contacts to the corn beef:

| Example | Description of Electrical Energy | Result of Electrical Resistance Cooking |
|---|---|---|
| LXII | Primary voltage of 115 volts stepped up to 375 volts, applied for a period of 15 seconds/6–9 amperes. | Corn beef anf bun very, very hot but arcing at 7 seconds. |
| LXIII | Primary voltage of 115 volts stepped up to 370 volts, applied for a period of 6 seconds/6.2–9.5 amperes. | Corn beef and bun very hot and cooked; no arcing. |
| LXIV | Primary voltage of 115 volts stepped up to 375 volts, applied for a period of 6 seconds/3.2–4.2 amperes. (Only 1 slice of corn beef on bun used). | Corn beef hot and cooked; no arcing. |

EXAMPLE LXV

A six inch by three-quarter inch beef frankfurter is coated at each end to the extend of one inch with a warm aqueous solution of 2% agar solution but not containing any ionized species (e.g., sodium chloride). After setting of the gel by cooling the frankfurter is then placed in a bun and the combination frankfurter and bun is placed in a container having electrical contacts attached thereto and connected to a source of electrical energy as illustrated in FIG. 4. Over a period of 18 seconds, a primary voltage of 115 volts stepped up to 340 volts is applied to the electrical contacts from the electrical energy source which results in a flow of from 1.2 up to 3.4 amperes. The electrical contacts, during this time, are in direct contact with those surfaces of the frankfurter that are coated with the agar. No cooking of the frankfurter took place. A similar experiment is carried out with the exception that instead of coating the frankfurter with the 2% agar solution, the agar solution is applied to the electrical contacts over the surface thereof that will be in contact with the frankfurter. Again, no cooking takes place.

What is claimed is:

1. A packaged food, for cooking the food therein, wherein a container encloses an edible sandwich type food, said packaged food comprising:
   a. An electrically low conducting food having high electrical resistivity;
   b. An electrically high conducting food disposed in contact with and substantially surrounded by said low conducting food;
   c. Said high conducting food having at least two diametrically opposite high conducting food portions extending outwardly beyond said low conducting food, each of which portion has a substantially solid external surface;
   d. In common intimate contact with at least a part of each of said external surfaces of high conducting food; an electrically high conducting composition and at least two electrical contacts, said electrically high conducting composition forming a continuous phase and coated onto and being an integral part of each of said substantially solid external surfaces comprising a combination of:
      i. a gel material selected from the group consisting of agar, xanthan gum, tragacanth, guar gum and gum arabic; and
      ii. an edible non-toxic substantially ionized species selected from the group consisting of sodium chloride, potassium chloride, ammonium chloride, sodium iodide, potassium iodide, magnesium chloride, sodium glutamate, potassium glutamate, sodium alginate, potassium alginate, ammonium alginate, magnesium alginate, calcium alginate, sodium bicarbonate, potassium bicarbonate, magnesium bicarbonate, calcium bicarbonate, sodium nitrate, potassium nitrate, sodium nitrite and potassium nitrite;
   said composition being positioned to make intimate contact between the electrical contacts and the substantially solid surface of said electrially high conducting food thereby acting to eliminate arcing during the electrical resistance cooking of the high conducting food;
   e. A hollow thermal insulating substantially moisture impervious container which contains and encloses said electrically low and high conducting foods, said container being capable of existing in a closed position and in an open position, said container comprising two sections having substantially conterminous edges, a first section and a second section articulating said first section, said first section and said second section having mutually substantially continuous conterminous edges, at least one of said sections having an internal surface designed to fixedly hold said high conducting food over those portions of the external surfaces of said high conducting food which are in intimate contact with said electrically high conducting composition and said electrical contact when the container is in a closed position; at least one of said container sections has substantially diametrically opposite internal surfaces which are conterminous with the external surfaces of said diametrically opposite high conducting food portions; and the electrical contacts extend outwardly from said container, said electrical contacts having electrically conducting ends external to said container, said ends being designed to make the electrical contact with an electrical energy source when said container is in a closed position.

2. The packaged food product of claim 1 wherein the ratio of gel material to edible non-toxic substantially ionized species in said electrically high conducting composition is from 1:20 up to 20:1.

3. The packaged food product of claim 1 wherein the electrically high conducting composition comprises:
   i. Agar; and
   ii. Sodium chloride 4. The packaged food product of claim 1 wherein the electrically high conducting composition comprises:
   i. Tragacanth; and
   ii. Sodium chloride.

5. The packaged food product of claim 1 wherein said first section of said container and said second section of said container have mutually substantially continuous co-extensive edges which edges are interrupted at the proximate regions of said substantially diametrically opposite high conducting food portions such that discreet container openings exist at said proximate regions whereby said electrical contacts have means of egress from said container when said container is in a closed position.

6. The packaged food product of claim 1 wherein each of said electrical contacts is an electrically conducting foil section.

7. The packaged food product of claim 1 wherein the electrically high conducting food is also thermally high conducting.

8. The packaged food product of claim 1 wherein the electrically high conducting food has a resistivity in the range of from 1 up to 50 ohm inches over a range of temperature from 30° F up to 250° F.

9. The packaged food product of claim 1 wherein the high conducting food is a hamburger.

10. The packaged food product of claim 1 wherein the said first section and said second section of said hollow container are hinged to one another.

11. The packaged food product of claim 1 wherein said electrical contacts comprise aluminum metallizing adhering to a major portion of the internal surface of one of the sections of the container which surface is designed to fixedly hold the food over those portions of the surfaces of the surface of said food which are in intimate contact with said electrically high conducting composition and said aluminum metallizing.

12. The packaged food product of claim 1 wherein said electrically conducting foil sections has a portion thereof in substantially total contact with said substantially diametrically opposite external surfaces of said high conducting food portions, the ratio of the surface area of contacted high conducting food portions to surface area of non-contacted high conducting food portions being from 1:50 up to 1:4.

13. The packaged food product of claim 12 having such intimate contact between said electrically conducting foil sections and said substantially diametrically opposite external surfaces of high conducting food portions whereby when an electrical current in the range of from 1.0 up to 10.0 amperes and from 100 up to 500 volts is applied for a period of time of from 3 up to 20 seconds to electrical conducting foil, the food substance in said packaged food product is heated internally such that the average temperature of said high conducting food after heating is initially in the range of from 140° F up to 212° F, and the average temperature range of said low conducting food is after heting initially in the range of from 100° F up to 160° F, and until about 50 minutes after heating the average temperature of said high conducting food is in the range of from 100° F up to 150° F, and the average temperature of said low conducting food is from 90° F up to 130° F.

14. The packaged food product of claim 1 wherein the high conducting food is a sausage.

15. The packaged food product of claim 14 wherein the sausage is a frankfurter.

* * * * *